(12) United States Patent
Popovic

(10) Patent No.: US 11,213,364 B2
(45) Date of Patent: Jan. 4, 2022

(54) IMAGE GUIDED MOTION SCALING FOR ROBOT CONTROL

(71) Applicant: KONINKLIJKE PHILIPS N.V., Eindhoven (NL)

(72) Inventor: Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 307 days.

(21) Appl. No.: 16/467,080

(22) PCT Filed: Dec. 5, 2017

(86) PCT No.: PCT/EP2017/081423
§ 371 (c)(1),
(2) Date: Jun. 6, 2019

(87) PCT Pub. No.: WO2018/104252
PCT Pub. Date: Jun. 14, 2018

(65) Prior Publication Data
US 2019/0307524 A1    Oct. 10, 2019

Related U.S. Application Data

(60) Provisional application No. 62/430,994, filed on Dec. 7, 2016.

(51) Int. Cl.
*A61B 34/00* (2016.01)
*A61B 34/37* (2016.01)
(Continued)

(52) U.S. Cl.
CPC ............ *A61B 34/77* (2016.02); *A61B 34/30* (2016.02); *A61B 34/37* (2016.02); *B25J 9/1697* (2013.01)

(58) Field of Classification Search
CPC ......... A61B 34/77; A61B 34/37; A61B 34/30; B25J 9/1697
(Continued)

(56) References Cited

U.S. PATENT DOCUMENTS 5,382,885 A    1/1995  Salcudean
6,424,885 B1 *  7/2002  Niemeyer ............... A61B 34/70
                                                600/109
(Continued)

FOREIGN PATENT DOCUMENTS

KR    20120068597    6/2012
WO    2013/018983    2/2013
(Continued)

OTHER PUBLICATIONS

International Search Report and Written Opinion dated Apr. 13, 2018 for International Application No. PCT/EP2017/081423 filed Dec. 5, 2017.

*Primary Examiner* — Jaime Figueroa

(57) ABSTRACT

A image guided motion scaled surgical robotic system (160) employs a surgical robotic arm (168) and an image guided motion scaled surgical controller (162). In operation, responsive to an input signal indicative of a user defined motion of the surgical robotic arm (168) within an anatomical region, the image guided motion scaled surgical controller (162) controls an actuated motion of the surgical robotic arm (168) within the anatomical region based on a map (164) of a motion scale delineated within an imaging of the anatomical region.

20 Claims, 15 Drawing Sheets

(51) Int. Cl.
*A61B 34/30* (2016.01)
*B25J 9/16* (2006.01)

(58) Field of Classification Search
USPC .................................................. 700/245–264
See application file for complete search history.

(56) References Cited

U.S. PATENT DOCUMENTS

| | | | | |
|---|---|---|---|---|
| 6,468,265 | B1* | 10/2002 | Evans | A61B 34/32 600/103 |
| 7,083,571 | B2 | 8/2006 | Yang | |
| 8,155,479 | B2* | 4/2012 | Hoffman | H04N 13/383 382/276 |
| 9,615,886 | B2 | 4/2017 | Popovic | |
| 9,888,973 | B2* | 2/2018 | Olson | A61B 34/71 |
| 10,548,679 | B2* | 2/2020 | Carlson | A61B 34/35 |
| 2004/0116906 | A1* | 6/2004 | Lipow | A61B 34/70 606/1 |
| 2007/0083098 | A1 | 4/2007 | Stern | |
| 2008/0255505 | A1* | 10/2008 | Carlson | A61B 34/37 604/95.04 |
| 2009/0036902 | A1* | 2/2009 | DiMaio | A61B 34/30 606/130 |
| 2010/0168763 | A1* | 7/2010 | Zhao | A61B 90/94 606/130 |
| 2010/0274087 | A1* | 10/2010 | Diolaiti | A61B 90/37 600/118 |
| 2010/0331858 | A1* | 12/2010 | Simaan | A61B 34/30 606/130 |
| 2011/0105898 | A1* | 5/2011 | Guthart | A61B 34/35 600/437 |
| 2012/0185099 | A1* | 7/2012 | Bosscher | G05B 19/427 700/264 |
| 2014/0018819 | A1* | 1/2014 | Raj | A61B 90/60 606/130 |
| 2014/0148819 | A1 | 5/2014 | Inoue | |
| 2014/0347353 | A1 | 11/2014 | Popovic | |
| 2016/0191887 | A1* | 6/2016 | Casas | A61B 34/20 348/47 |
| 2016/0228204 | A1* | 8/2016 | Quaid | A61B 17/1703 |
| 2016/0314717 | A1* | 10/2016 | Grubbs | G09B 5/14 |
| 2017/0071681 | A1* | 3/2017 | Peine | A61B 34/30 |
| 2017/0265956 | A1* | 9/2017 | Carlson | A61B 34/70 |
| 2017/0367771 | A1* | 12/2017 | Tako | A61B 34/20 |
| 2018/0296285 | A1* | 10/2018 | Simi | B25J 3/04 |
| 2019/0090967 | A1* | 3/2019 | Guthart | A61B 34/37 |
| 2021/0106393 | A1* | 4/2021 | Simi | B25J 9/104 |

FOREIGN PATENT DOCUMENTS

| | | |
|---|---|---|
| WO | 2014121262 | 8/2014 |
| WO | 2016/028858 | 2/2016 |
| WO | 2016053657 | 4/2016 |
| WO | 2016133633 | 8/2016 |

\* cited by examiner

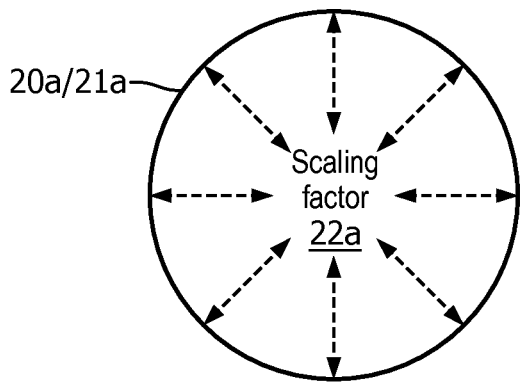 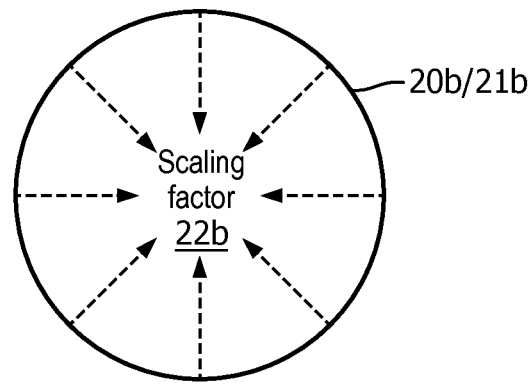
FIG. 2A  FIG. 2B
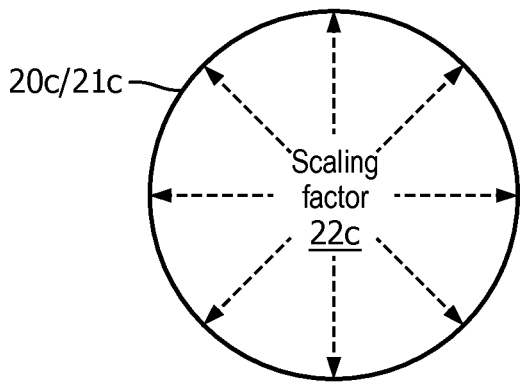 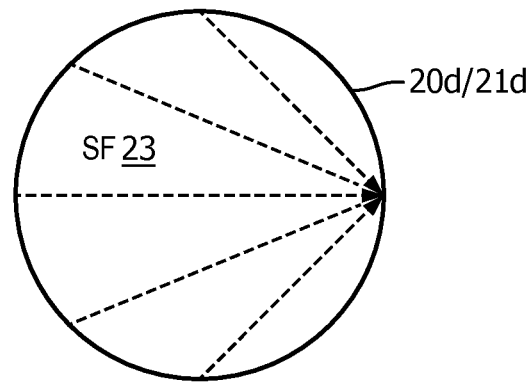
FIG. 2C  FIG. 2D
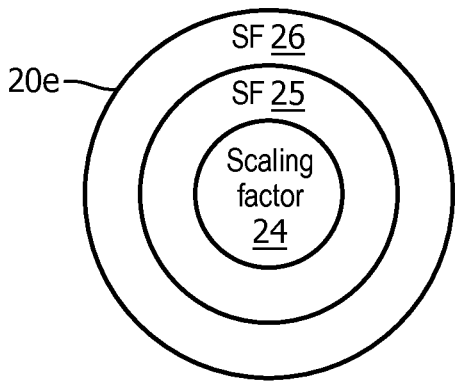 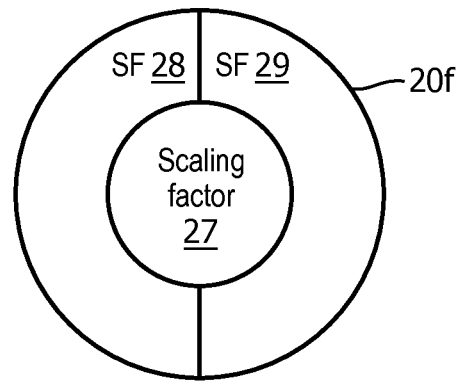
FIG. 2E  FIG. 2F

IMAGE GUIDED MOTION SCALING FOR ROBOT CONTROL

CROSS REFERENCE TO RELATED APPLICATIONS

This application is the U.S. National Phase application under 35 U.S.C. § 371 of International Application No. PCT/EP2017/081423 filed Dec. 5, 2017, published as WO 2018/104252 on Jun. 14, 2018, which claims the benefit of U.S. Provisional Patent Application No. 62/430,994 on Dec. 7, 2016. These applications are hereby incorporated by reference herein.

FIELD OF THE INVENTION

The inventions of the present disclosure generally relate to surgical robotic systems incorporating motion scales within the control of one or more surgical robotic arms (e.g., the da Vinci® Surgical System, the Raven Robotic Surgical System, the Sport™ Surgical System, the Flex™ Robotic System, etc.). The inventions of the present disclosure more particularly relate to improving such surgical robotic systems by incorporating an image guided motion scaling within the control of surgical robotic arm(s).

BACKGROUND OF THE INVENTION

Surgical robotic systems today are controlled from a surgeon console. More particularly, an operator moves handles on the console whereby a signal from the handles is interpreted and translated into the motion of a surgical robotic arm. This motion may be scaled so that a motion of a robot end-effector is smaller or larger than the motion of the handles or operator's hands. Currently, the scaling factor is defined by the surgical robotic system or by the operator of the system. For example, the operator may define the scaling factor as 5:1, which means a motion defined by the handles of the surgeon console is reduced 5× for the corresponding motion of the robot end-effector.

The scaling factor facilitates an improvement in a precision of a surgical robotic procedure by allowing console operators to perform very delicate procedures (e.g., suturing a small vessel) with large handle motion that is more intuitive and by scaling down any operator tremor applied to the handles.

Historically, the scaling factor may be effectuated via a voice recognition system, control buttons or the like, and may be set differently for different surgical robotic arms and along different directions. Nonetheless, a setting of a scaling factor is subjective and it is fixed until the console operator decides to modify the scaling factor. Additionally, the current subjective setting of a scaling factor fails to effectively account for the surgical environment and is therefore independent of a proximity of a robotic end-effector to critical structures or tissue or to other robotic arms.

Furthermore, one issue is a constant scaling factor may lead to surgical complications. For example, if the scaling factor is set to amplify a motion of a robotic arm and a console operator gets close to a forbidden zone of an anatomical region, then a reaction time of the console operator may not be sufficient to stop or slow down the approach of the surgical robotic arm to the forbidden zone, which may lead to injury. Also, in some cases, another issue is a surgical task may require fine motion in one area of the anatomical region and fast motion in another area of the anatomical region. For example, if tissue is to be removed (e.g., resection of a tumor or milling of bone), then a fast, large motion may be desirable in free space of the anatomical region while a fine or slow motion might be required close to the tissue boundaries. Clearly, frequent changes of the scaling factor by the console operator to address these issues may distract from the surgical robotic task.

SUMMARY OF THE INVENTION

To improve upon motion scaling incorporated within a control of surgical robotic arms within a surgical coordinate space encircling an anatomical region, the present disclosure provides inventions for defining a motion scale of a surgical robotic arm from a pre-operative imaging and/or an intra-operative imaging of the anatomical region (e.g., a endoscopic/laparoscopic image, an X-ray image, a computed-tomography image, an ultrasound image, a magnetic resonance image, etc.). The motion scale may be based on any parameter related to the motion of a surgical robotic arm within the surgical coordinate space including, but not limited to, a positioning and a speed of the surgical robotic arm within the surgical coordinate space. The improvement by the inventions of the present disclosure is the motion scale will depend on the environment in which the surgical robotic arm is operating and allow for improved handling by facilitating a reduction in a risk to patient injury and a reduction in surgical procedure time.

For purposes of describing and claiming the inventions of the present disclosure:

(1) the term "motion scale" broadly encompasses, as exemplary shown herein, a planar area or a volumetric area mapped within an imaging of an anatomical region whereby a scaling factor is applied to a user defined motion of a surgical robotic arm within the anatomical region to thereby control an actuated motion of the surgical robotic arm within the anatomical region with the actuated motion of the surgical robotic arm being an attenuation or an amplification of the user defined motion of the surgical robotic arm within the anatomical region;

(2) the terms "user defined motion" and "actuated motion" are to be interpreted as known in the art of the present disclosure and exemplary shown herein;

(3) the term "image guided motion scaled surgical robotic system" broadly encompasses all surgical robotic systems, as known in the art of the present disclosure and hereinafter conceived, incorporating the inventive principles of the present disclosure for defining a motion scale of a surgical robotic arm from a pre-operative imaging and/or an intra-operative imaging of the anatomical region (e.g., a endoscopic/laparoscopic image, an X-ray image, a computed-tomography image, an ultrasound image, a magnetic resonance image, etc.). Examples of known surgical robotic systems include, but are not limited to, the da Vinci® Surgical System, the Raven Robotic Surgical System, the Sport™ Surgical System and the Flex™ Robotic System;

(4) the term "image guided motion scaled robot control method" broadly encompasses all methods of controlling a surgical robotic system, as known in the art of the present disclosure and hereinafter conceived, incorporating the inventive principles of the present disclosure defining a motion scale of a surgical robotic arm from a pre-operative imaging and/or an intra-operative imaging of the anatomical region (e.g., a endoscopic/laparoscopic image, an X-ray image, a computed-tomography image, an ultrasound image, a magnetic resonance image, etc.);

(5) the term "image guided motion scaled robot controller" broadly encompasses all structural configurations of an application specific main board or an application specific integrated circuit housed employed within an image guided motion scaled surgical robotic system of the present disclosure for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), interface(s), bus(es), slot(s) and port(s);

(6) the term "application module" broadly encompasses a component of the image guided motion scaled robot controller consisting of an electronic circuit and/or an executable program (e.g., executable software and/or firmware stored on non-transitory computer readable medium(s)) for executing a specific application; and (7) the terms "signal", "data" and "command" broadly encompasses all forms of a detectable physical quantity or impulse (e.g., voltage, current, or magnetic field strength) as understood in the art of the present disclosure and as exemplary described herein for communicating information and/or instructions in support of applying various inventive principles of the present disclosure as subsequently described herein. Signal/data/command communication between components of the present disclosure may involve any communication method, as known in the art of the present disclosure and hereinafter conceived, including, but not limited to, data/command transmission/reception over any type of wired or wireless medium/datalink and a reading of signal/data/commands uploaded to a computer-usable/computer readable storage medium.

One embodiment of the inventions of the present disclosure is an image guided motion scaled surgical robotic system employing a surgical robotic arm and an image guided motion scaled robot controller. In operation, responsive to an input signal indicative of a user defined motion of the surgical robotic arm within an anatomical region, the image guided motion scaled robot controller controls an actuated motion of the surgical robotic arm within the anatomical region based on a map of a motion scale delineated within an imaging of the anatomical region.

A second embodiment of the inventions of the present disclosure is the image guided motion scaled robot controller employing application modules including a motion vector generator and a surgical robotic arm actuator.

In operation, the motion vector generator generates a motion vector signal responsive to an input signal indicative of a user defined motion of the surgical robotic arm within the anatomical region, the motion vector signal being indicative of an actuated motion of a surgical robotic arm within the anatomical region. The generation of the motion vector signal by the motion vector generator may be based on the map of the motion scale delineated within the imaging of the anatomical region.

Further in operation, responsive to the generation of the motion vector signal by the motion vector generator, the surgical robotic arm actuator structurally generates actuation commands instructive of the actuated motion of the surgical robotic arm within the anatomical region. The generation of the actuation commands by the surgical robotic arm actuator may be based on the map of the motion scale delineated within the imaging of the anatomical region.

A third form embodiment of the inventions of the present disclosure is an image guided motion scaled robot control method implemented by the image guided motion scaled surgical robotic system. The image guided motion scaled robot control method involves the image guided motion scaled robot controller receiving an input signal indicative of a user defined motion of the surgical robotic arm within the anatomical region. The image guided motion scaled robot control method further involves the image guided motion scaled robot controller, responsive to the input signal, controlling a actuated motion of the surgical robotic arm within the anatomical region based on the map of the motion scale delineated within the imaging of the anatomical region.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

BRIEF DESCRIPTION OF THE DRAWINGS

FIGS. 2A-2F illustrate exemplary scaling factors in accordance with the inventive principles of the present disclosure.

DETAILED DESCRIPTION OF THE PREFERRED EMBODIMENTS

Figure 1A:
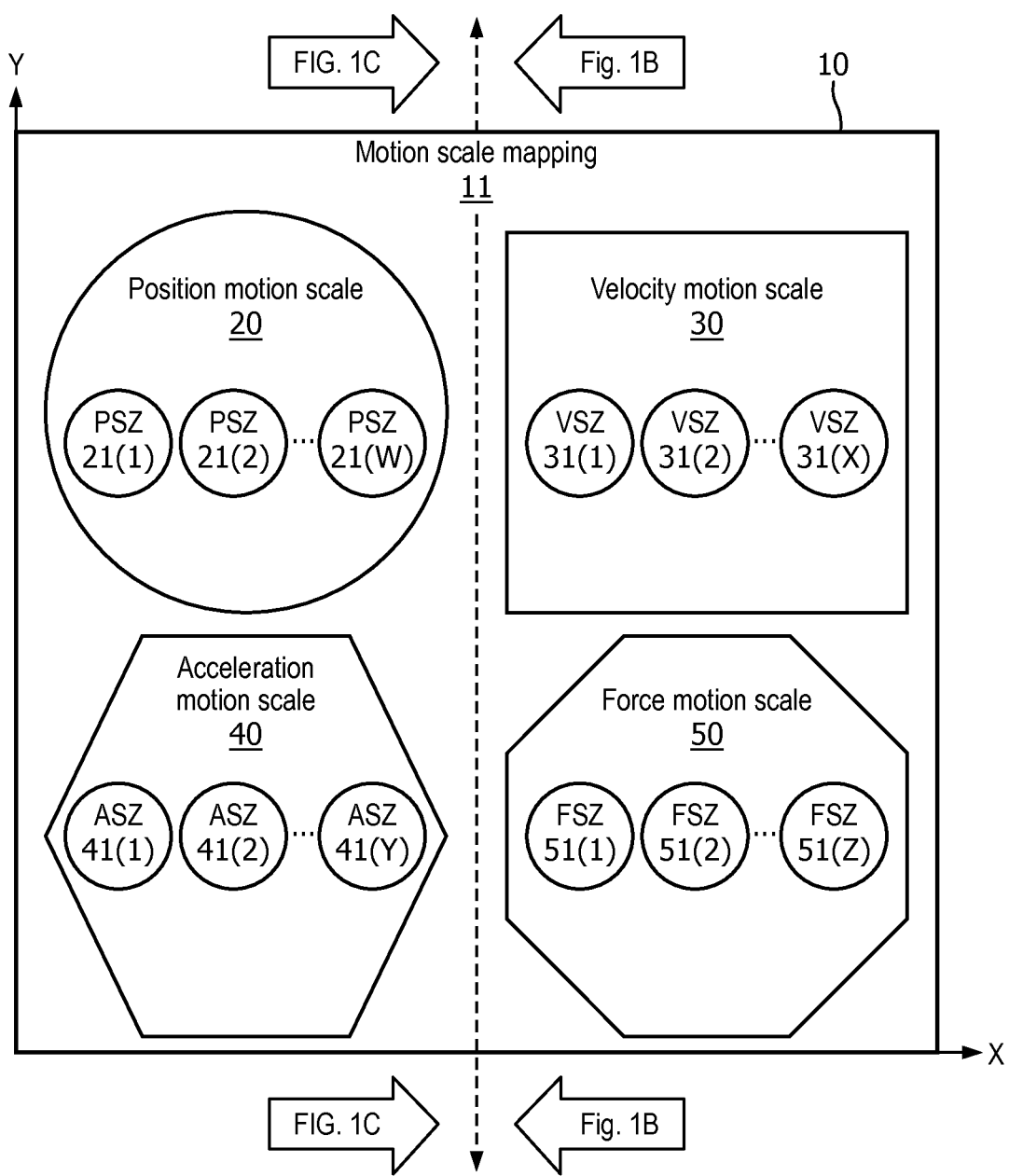
FIGS. 1A-1C illustrate exemplary embodiments of a mapping of motion scales within an imaging coordinate space in accordance with the inventive principles of the present disclosure.

As will be further described herein, a motion scale of the present disclosure encompasses a planar area or a volumetric area mapped within an imaging of an anatomical region whereby a scaling factor is applied to a user defined motion of a surgical robotic arm within the anatomical region to thereby control an actuated motion of the surgical robotic arm within the anatomical region with the actuated motion of the surgical robotic arm being an attenuation or an amplification of the user defined motion.

More particularly, a motion scale of the present disclosure includes one or more scaling factors. A scaling factor of the present disclosure may be a ratio of $SF_{ATT}$:1 quantifying an attenuation of the user defined motion in controlling the motion of the surgical robotic arm within the anatomical region, or may be ratio of 1:$SF_{AMP}$ quantifying an amplification of the user defined motion in controlling the motion of the surgical robotic arm within the anatomical region.

For example, a scaling factor of 5:1 quantifies an attenuation of the user defined motion by 5× in controlling the motion of the surgical robotic arm within the anatomical region, and a scaling factor of 1:5 quantifies an amplification of the user defined motion by 5× in controlling the motion of the surgical robotic arm within the anatomical region.

In practice, a motion scale of the present disclosure may have a single scaling factor for an entirety of the planar area or the volumetric area within the imaging coordinate space.

Also in practice, the single scaling factor may be a fixed attenuation ratio or a fixed amplification ratio throughout the entirety of the planar area or the volumetric area. Alternatively, the single scaling factor may be a variable attenuation ratio or a variable amplification ratio throughout the entirety of the of the planar area or the volumetric area within the imaging coordinate space.

For example, the scaling factor may quantify a positive sloping or a negative sloping attenuation or amplification of the user defined motion across the planar area or the volumetric area in controlling the motion of the surgical robotic arm within the surgical coordinate space.

By further example, the scaling factor may quantify a conditional attenuation or a conditional amplification of the user defined motion across the planar area or the volumetric area in controlling the motion of the surgical robotic arm within the anatomical region based on characteristics of the surgical environment including, but not limited to, (1) an increase or a decrease in the scaling factor as a function of a positioning of one or more surgical robotic arms within the anatomical region relative to a positioning of an anatomical structure illustrated within the imaging of the anatomical region, and (2) an increase or a decrease in the scaling factor as a function of a relative positioning of two surgical robotic arms within the anatomical region.

Further in practice, a motion scale of the present disclosure may encompass a zoning of the planar area or the volumetric area within the imaging coordinate space whereby each zone has a different scaling factor that may be fixed or variable as previously described herein.

Also in practice, a designated technique of the present disclosure for mapping a motion scale into the image coordinate space may be in accordance with a particular type of surgical robotic procedure to be performed on the anatomical region and/or a particular type of imaging of the anatomical region (e.g., a endoscopic/laparoscopic image, an X-ray image, a computed-tomography image, an ultrasound image, a magnetic resonance image, etc.).

To facilitate an understanding of the inventions of the present disclosure, the following description of FIGS. 1-4 teaches basic inventive principles of a graphical delineation mapping of a motion scale within an imaging coordinate space in accordance with the inventive principles of the present disclosure. From this description of FIGS. 1-4, those having ordinary skill in the art will appreciate how to apply the inventive principles of the present disclosure to practice numerous and various embodiments of a graphical delineation mapping of a motion scale within an imaging coordinate space.

Generally, a motion scale in accordance with the inventive principles of the present disclosure may be derived from a graphical delineation of a mapping of the motion scale within an imaging coordinate space of the imaging of an anatomical region.

In practice, the graphical delineation may be performed in accordance with known image processing techniques for delineating graphical objects within an imaging coordinate space including, but not limited to, path planning techniques for delineating a planned surgical path within an imaging of the anatomical region.

For example, in one embodiment, a delineation of a mapping of the motion scale within the imaging of the anatomical region may be facilitated by a graphical user interface providing for a user delineation of a planar area or a volumetric area within the imaging of the anatomical region, particularly relative to any anatomical structure illustrated within or segmented from the imaging of the anatomical region.

Also in practice, the imaging of the anatomical region may be a two-dimensional ("2D") anatomical imaging or a three-dimensional ("3D") anatomical imaging performed during a pre-operative phase and/or an intra-operative phase of a surgical robotic procedure, and may be performed by any type of the imaging modality applicable to the surgical robotic procedure (e.g., a endoscopic/laparoscopic image, an X-ray image, a computed-tomography image, an ultrasound image, a magnetic resonance image, etc.).

Additionally in practice, a motion scale of the present disclosure may represent one or more parameters related to the motion of a surgical robotic arm within the anatomical region including, but not limited:

1. a scaling of a position of a user input device to a position of a surgical robotic arm;
2. a scaling of a velocity of the user input device to a velocity of a surgical robotic arm;
3. a scaling of an acceleration of the user input device to an acceleration of a surgical robotic arm; and
4. a scaling of a force/effort to move the user input device in terms of positioning, a velocity or an acceleration of the surgical robotic arm.

Figure 1B:
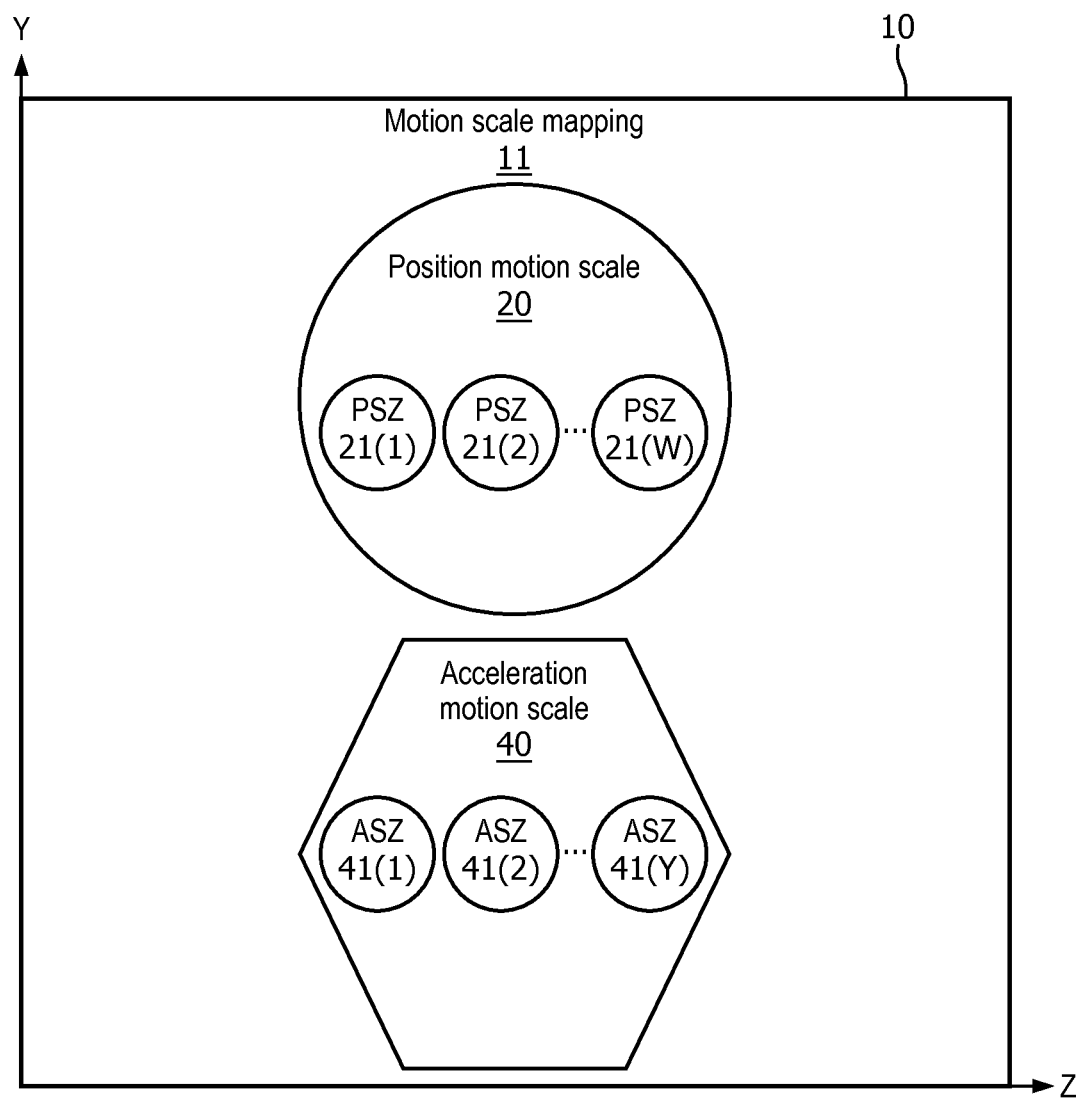
Figure 1C:
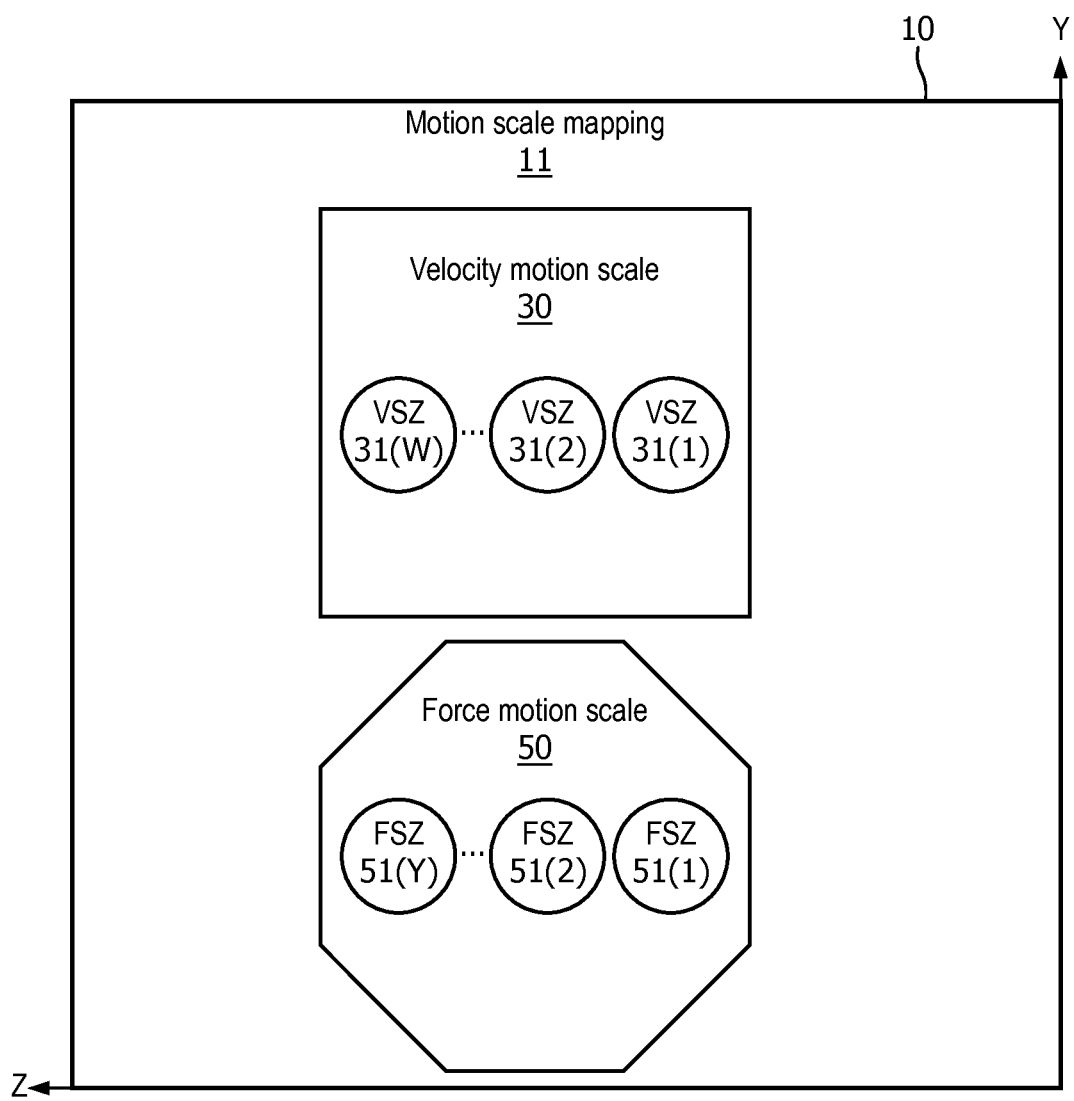

FIG. 1A illustrates motion scale mapping 11 of a plurality of motion scales 20, 30, 40, 50 of the present disclosure delineated within an anatomical image space 10 outlining an imaging of an anatomical region, of which anatomical structures of the anatomical region are not shown for clarity. While motion scales 20, 30, 40, 50 may encompass a planar area as shown in FIG. 1A for two-dimensional ("2D") imaging of the anatomical region (e.g., endoscopic/laparoscopic imaging or ultrasound imaging), motion scales 20, 30, 40, 50 may encompass a volumetric area as respectively shown in FIGS. 1B and 1C for three-dimensional ("3D") imaging (e.g., CT imaging, MRI imaging and X-ray imaging). Additionally, the planar arear or the volumetric area of a mapped motion scale of the present disclosure may have any geometric shape, regular or irregular, including, but not limited to, a circular shape of position motion scale 20 as shown in FIGS. 1A and 1B, a square shape of velocity motion scale 30 as shown in FIGS. 1A and 1C, a hexagonal shape of acceleration motion scale 40 as shown in FIGS. 1A and 1B and an octagonal shape of force motion scale 50 as shown in FIGS. 1A and 1C.

In practice, a user defined motion of a surgical robotic arm within an anatomical region is generated by a user input device of a surgical robotic arm as known in the art of the present disclosure (e.g., handle(s), joystick(s), roller ball(s), etc.). More particularly, the user input device communicates an input signal indicative of a motion parameter directed to controlling a motion of the surgical robotic arm within the anatomical region.

For an input signal indicative of a user defined positioning of a surgical robotic arm within an anatomical region ("positioning input signal"), position motion scale 20 provides a scaling of the positioning input signal to a positioning motion of a surgical robotic arm within the anatomical region. For example, the positioning input signal may indicate a translation, a rotation and/or a pivoting of the surgical robotic arm within the anatomical region whereby position motion scale 20 provides for an attenuation or an amplification of the indicated translation, a rotation and/or a pivoting of the surgical robotic arm within the anatomical region to thereby control a translation, a rotation and/or a pivoting of the surgical robotic arm within the surgical coordinate space encircling the anatomical region.

In practice, position motion scale 20 may include a single scaling factor that is fixed or variable throughout position motion scale 20. Alternatively, position motion scale may be divided into a W number of position scaling zones 21, W≥2, with each position scaling zone 21 having a different scaling factor that is fixed or variable throughout that particular position scaling zone 21. A size and a shape each position scaling zone 21 may be or may not be identical to another position scaling zone 21.

For an input signal indicative of a user defined velocity of a surgical robotic arm within an anatomical region ("velocity input signal"), velocity motion scale 30 provides a scaling of the velocity input signal to a velocity motion of the surgical robotic arm within the anatomical region. For example, the velocity input signal may indicate a desired velocity of a pre-defined translation, rotation and/or pivoting of the surgical robotic arm within the anatomical region whereby velocity motion scale 30 provides for an attenuation or an amplification of the indicated velocity of the pre-defined translation, rotation and/or pivoting of the surgical robotic arm within the anatomical region to thereby control the velocity of the pre-defined translation, rotation and/or pivoting of the surgical robotic arm within a surgical coordinate space encircling the anatomical region.

In practice, velocity motion scale 30 may include a single scaling factor that is fixed or variable throughout velocity motion scale 30. Alternatively, velocity motion scale may be divided into a X number of velocity scaling zones 31, X≥2, with each velocity scaling zone 31 having a different scaling factor that is fixed or variable throughout that velocity scaling zone 31. A size and a shape each velocity scaling zone 31 may be or may not be identical to another velocity scaling zone 31.

For an input signal indicative of a user defined acceleration of a surgical robotic arm within an anatomical region ("acceleration input signal"), acceleration motion scale 40 provides a scaling of the acceleration input signal to an acceleration motion of the surgical robotic arm within the anatomical region. For example, the acceleration input signal may indicate a desired acceleration of a pre-defined translation, rotation and/or pivoting of the surgical robotic arm within the anatomical region whereby acceleration motion scale 40 provides for an attenuation or an amplification of the indicated acceleration of the pre-defined translation, rotation and/or pivoting of the surgical robotic arm within the anatomical region to thereby control the acceleration of a pre-defined translation, rotation and/or pivoting of the surgical robotic arm within a surgical coordinate space encircling the anatomical region.

In practice, acceleration motion scale 40 may include a single scaling factor that is fixed or variable throughout acceleration motion scale 40. Alternatively, acceleration motion scale may be divided into a Y number of acceleration scaling zones 41, Y≥2, with each acceleration scaling zone 41 having a different scaling factor that is fixed or variable throughout that acceleration scaling zone 41. A size and a shape each acceleration scaling zone 41 may be or may not be identical to another acceleration scaling zone 41.

For the position input signal, the velocity input signal or the acceleration input signal, force motion scale 50 provides a scaling of the force applied to the user input device required to move the surgical robotic arm within a surgical coordinate space in accordance with the position input signal, the velocity input signal or the acceleration input signal. For example, force motion scale 50 provides for an attenuation or an amplification of the force applied to the user input device required to move the surgical robotic arm within a surgical coordinate space in accordance with the position input signal, the velocity input signal or the acceleration input signal.

In practice, force motion scale 50 may include a single scaling factor that is fixed or variable throughout force motion scale 50. Alternatively, force motion scale may be divided into a Z number of force scaling zones 51, Z≥2, with each force scaling zone 51 has a different scaling factor that is fixed or variable throughout that force scaling zone 51. A size and a shape each force scaling zone 51 may be or may not be identical to another force scaling zone 51.

FIGS. 2A-2F illustrates various exemplary scaling factors of mapped motion scales embodiments of the present disclosure. While FIGS. 2A-2F are described in the context of position motion scale 20 (FIG. 1), those having ordinary skill in the art will appreciate how to apply the inventive principles of the present disclosure to practice numerous and various embodiments of scaling factors of mapped motion scales embodiments of the present disclosure.

FIG. 2A illustrates a radial scaling factor 22a having a fixed attenuation or a fixed amplification of a user defined motion as symbolized by the bi-directional arrows within position motion scale 20a or a position scale zone 21a. For this example, the center of position motion scale 20a or position scale zone 21a may represent a targeted location or an entry location of the surgical robotic arm within an anatomical region.

FIG. 2B illustrates a radial scaling factor 22b having a variable attenuation of a user defined motion as symbolized by the uni-directional arrows within position motion scale 20b or a position scale zone 21b. For this example, the center of position motion scale 20b or position scale zone 21b may represent a targeted location of the surgical robotic arm within an anatomical region.

FIG. 2C illustrates a radial scaling factor 22c having a variable amplification of a user defined motion as symbolized by the uni-directional arrows within position motion scale 20c or a position scale zone 21c. For this example, the center of position motion scale 20c or position scale zone 21c may represent an entry location of the surgical robotic arm within an anatomical region.

FIG. 2D illustrates a chord scaling factor 23 having a variable amplification of a user defined motion as symbolized by the uni-directional arrows within position motion scale 20d or a position scale zone 21d. For this example, an endpoint of the chords scale 20d or position scale zone 21d may represent a targeted location of the surgical robotic arm within an anatomical region.

FIG. 2E illustrates a trio of concentric scaling factors 24-26 representative of three (3) scaling zones of a position motion scale 21e. Each scaling factor 24-26 has a different fixed or variable attenuation or amplification of a user defined motion. For this example, the center of the position scaling zones may represent a targeted location or an entry location of the surgical robotic arm within an anatomical region.

FIG. 2F illustrates three (3) scaling zones of a position motion scale 21f including a scaling factor 27 encircled by semi-hemisphere scaling factors 28 and 29. Each scaling factor 27-29 has a different fixed or variable attenuation or amplification of a user defined motion. For this example, the center of the position scaling zones may represent a targeted location or an entry location of the surgical robotic arm within an anatomical region.

In practice, a surgical robotic procedure may involve a pre-operative endoscopic view and an intra-operative endoscopic view of an anatomical structure. The following is a description of an image guided motion scaled robot control method of the present disclosure involving a pre-operative endoscopic view and an intra-operative endoscopic view of an anatomical structure.

Figure 3A:
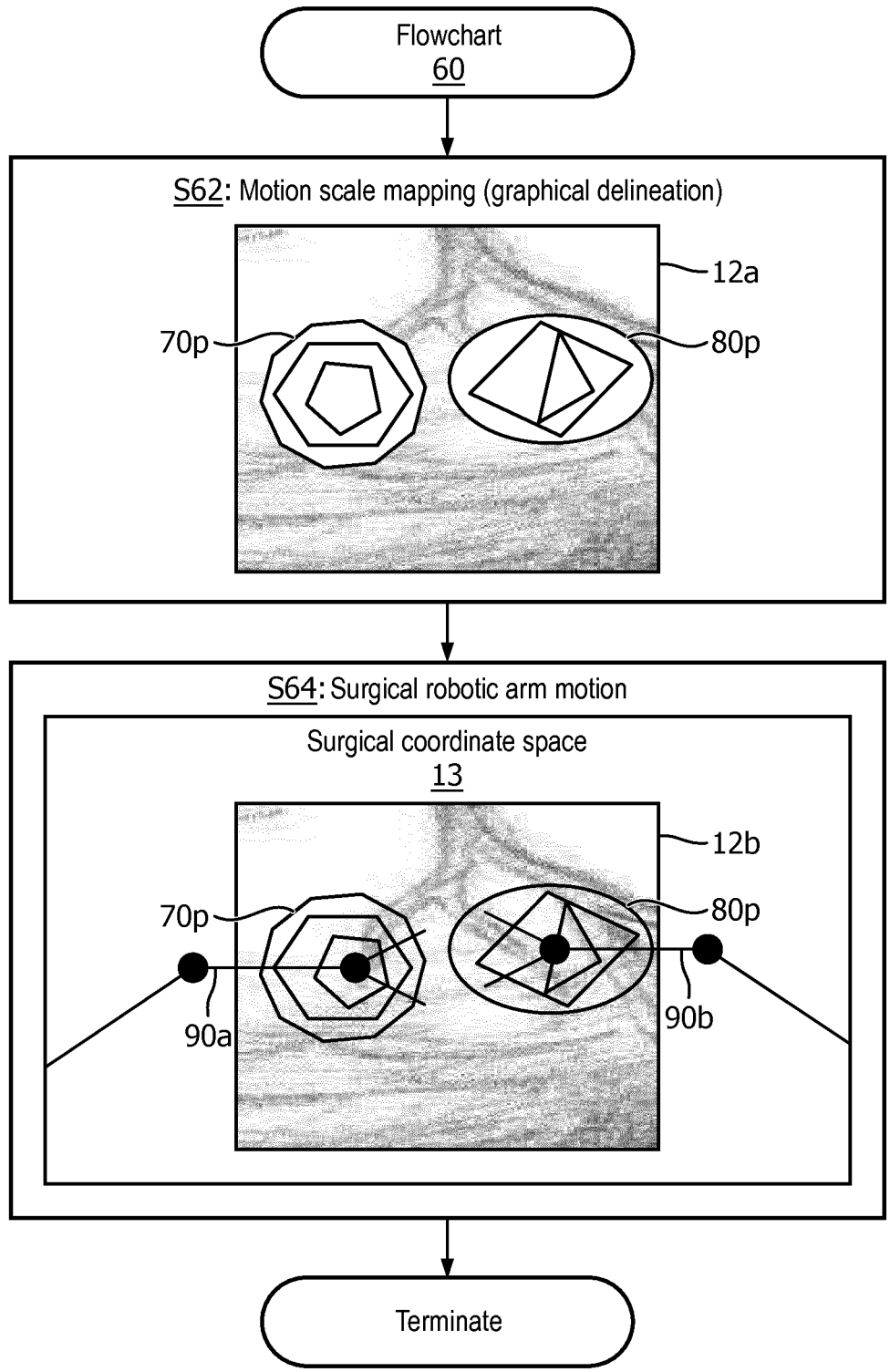
FIG. 3A illustrates a flowchart representative of a graphical delineation mapping of a motion scale within a two-dimensional ("2D") imaging coordinate space in accordance with the inventive principles of the present disclosure.

Referring to FIG. 3A, a flowchart 60 represents an image guided motion scaled robot control method of the present disclosure involving an a pre-operative endoscopic view 12a and an intra-operative endoscopic view 12b of a heart.

Generally, in a pre-operative phase of the surgical robotic procedure, a surgical robotic arm holding an endoscope is positioned via a user input device within a surgical coordinate space encircling a cardiac region to acquire pre-operative endoscopic view 12a of the heart. Thereafter, for an intra-operative phase of the surgical robotic procedure, the endoscope is held in or repositioned to the same pre-operative position to acquire an intra-operative endoscopic view 12b of a heart.

Specifically, a stage S62 of flowchart 60 encompasses a motion scale mapping of a motion scale 70p and a motion scale 80p within an image coordinate space of pre-operative endoscopic view 12a of the heart. To this end, as known in the art of the present disclosure, stage S62 may involve a calibration of the endoscope holding surgical robotic arm and a field of view of the endoscope, and a tracking of the surgical robotic arm within the surgical coordinate space (e.g., an electromagnetic tracking, an optical tracking, a Fiber-Optic RealShape ("FORS") sensor tracking, and encoded joint tracking). From the calibration and tracking, the endoscope holding surgical robotic arm is actuated via a user input device to a desired field of view of the endoscope for the acquisition of pre-operative endoscopic view 12a of the heart.

Figure 3B:
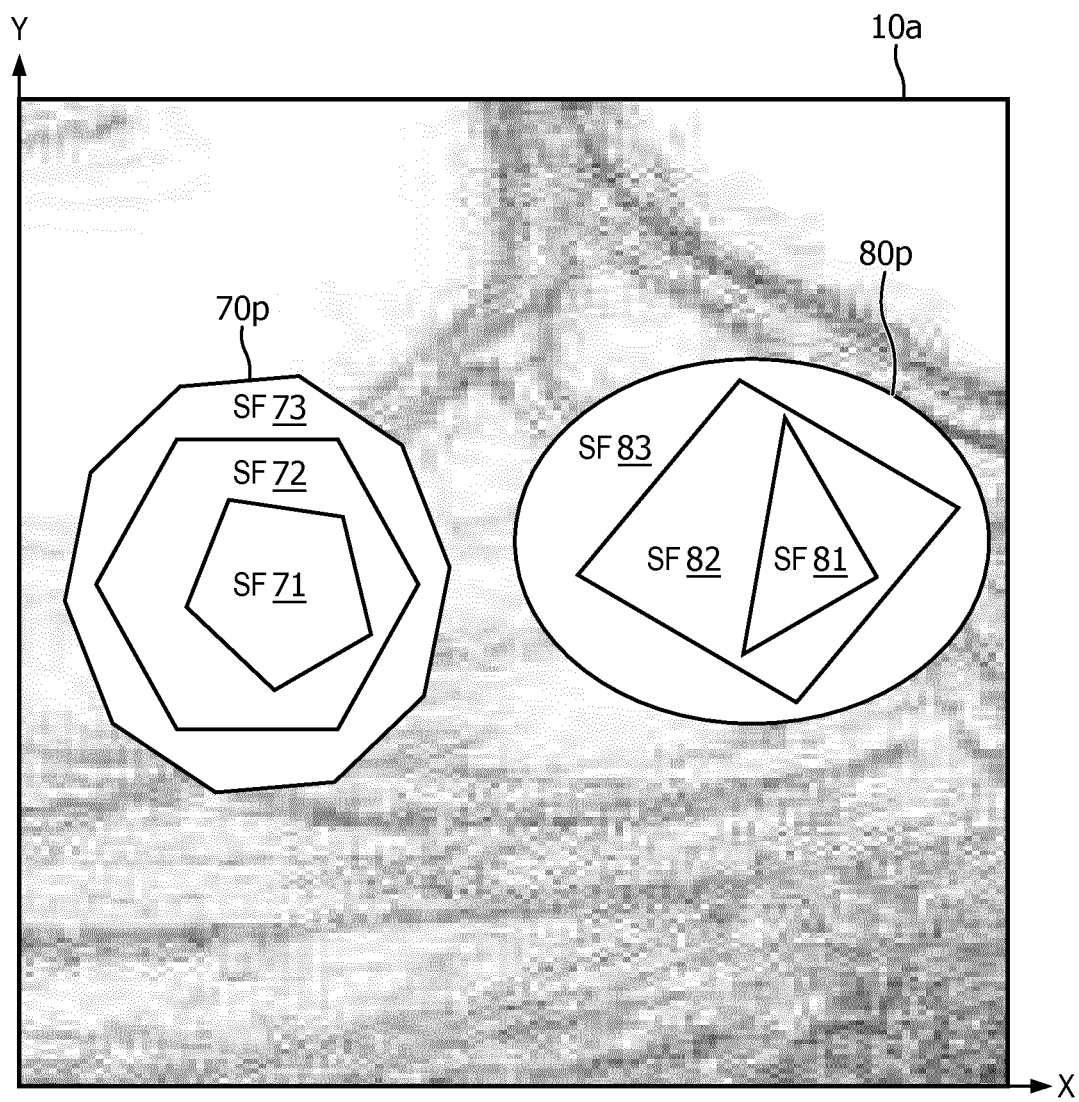
FIG. 3B illustrates an exemplary a graphical delineation mapping of a motion scale within a 2D imaging coordinate space in accordance with the inventive principles of the present disclosure.

Once positioned, a graphical user interface (not shown) is provided for allowing a graphical delineation of motion scale 70p and motion scale 80p within an image coordinate space 10a outlining pre-operative endoscopic view 12a of the heart as best shown in FIG. 3B. Referring to FIG. 3B, motion scale 70p includes three (3) zones of scaling factors 71-73 covering a planar area as shown relative to the heart and motion scale 80p includes three (3) zones of scaling factors 81-83 covering a planar area as shown relative to the heart. While motion scale 70p and motion scale 80p are delineated covering planar areas, in practice, motion scale 70p and motion scale 80p may be positioned within the field of view of the endoscope at any depth, such as, for example, adjacent the heart as identified in pre-operative endoscopic view 12a of heart 12. Alternatively, motion scale 70p and motion scale 80p may cover a volumetric area extending through the field of view of the endoscope.

Referring back to FIG. 3A, a stage S64 of flowchart 60 encompasses an actuation of a pair of surgical robotic arms 90a and 90b via a user input device within a 3D surgical coordinate space 13 encircling the cardiac region. Specifically, prior to entering into the field of view of the endoscope, motion of end-effectors of surgical robotic arms 90a and 90b within surgical coordinate space 13 in accordance with a default motion setting is tracked (e.g., an electromagnetic tracking, an optical tracking, a FORS sensor tracking, and encoded joint tracking)

As surgical robotic arms 90a and 90b appear in intra-operative endoscopic view 12b, motion scales 70p and 80p are applied to the default motion setting depending on the tracked positions of the end-effectors of surgical robotic arms 90a and 90b within surgical coordinate space 13 or image coordinate space 12b.

Also in practice, a surgical robotic procedure may involve a pre-operative scanning and an intra-operative endoscopic view of an anatomical structure. The following is a description of an image guided motion scaled robot control method of the present disclosure involving a pre-operative scanning and an intra-operative endoscopic view of an anatomical structure.

Figure 4A:
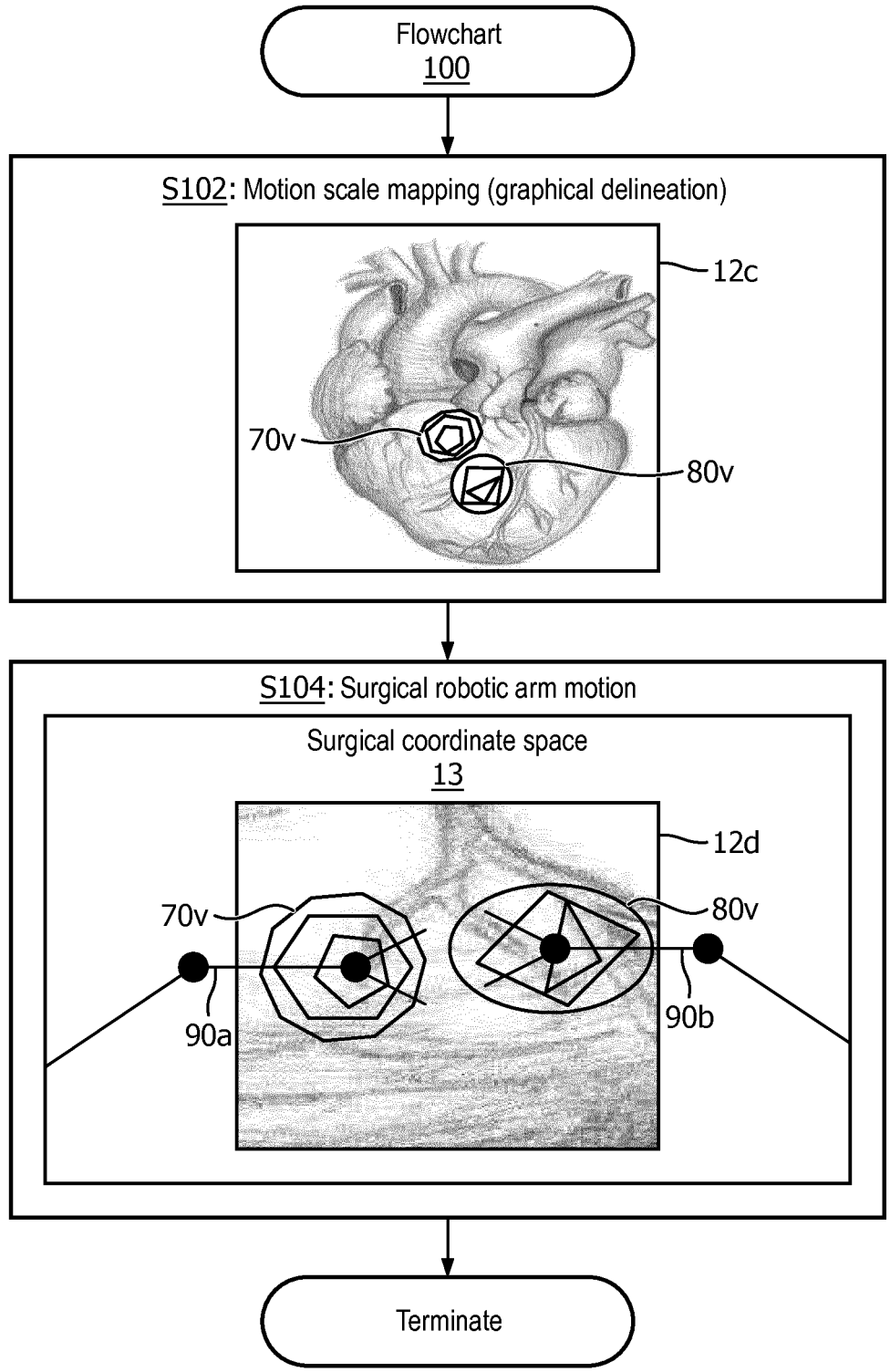
FIG. 4A illustrates a flowchart representative of a graphical delineation mapping of a motion scale within a three-dimensional ("3D") imaging coordinate space in accordance with the inventive principles of the present disclosure.

Referring to FIG. 4A, a flowchart 100 represents an image guided motion scaled robot control method of the present disclosure involving a pre-operative scan 12c and an intra-operative endoscopic view 12d of a heart.

Generally, in a pre-operative phase of the surgical robotic procedure, an imaging system is used to scan the cardiac region to acquire pre-operative scan 12c of the heart (e.g., a CT, MRI or X-ray scan). Thereafter, in an intra-operative phase of the surgical robotic procedure, an endoscope may be positioned to acquire an intra-operative endoscopic view 12d of a heart whereby intra-operative endoscopic view 12d is fused with pre-operative scan 12c of the heart for display purposes as known in the art of the present disclosure.

Figure 4B:
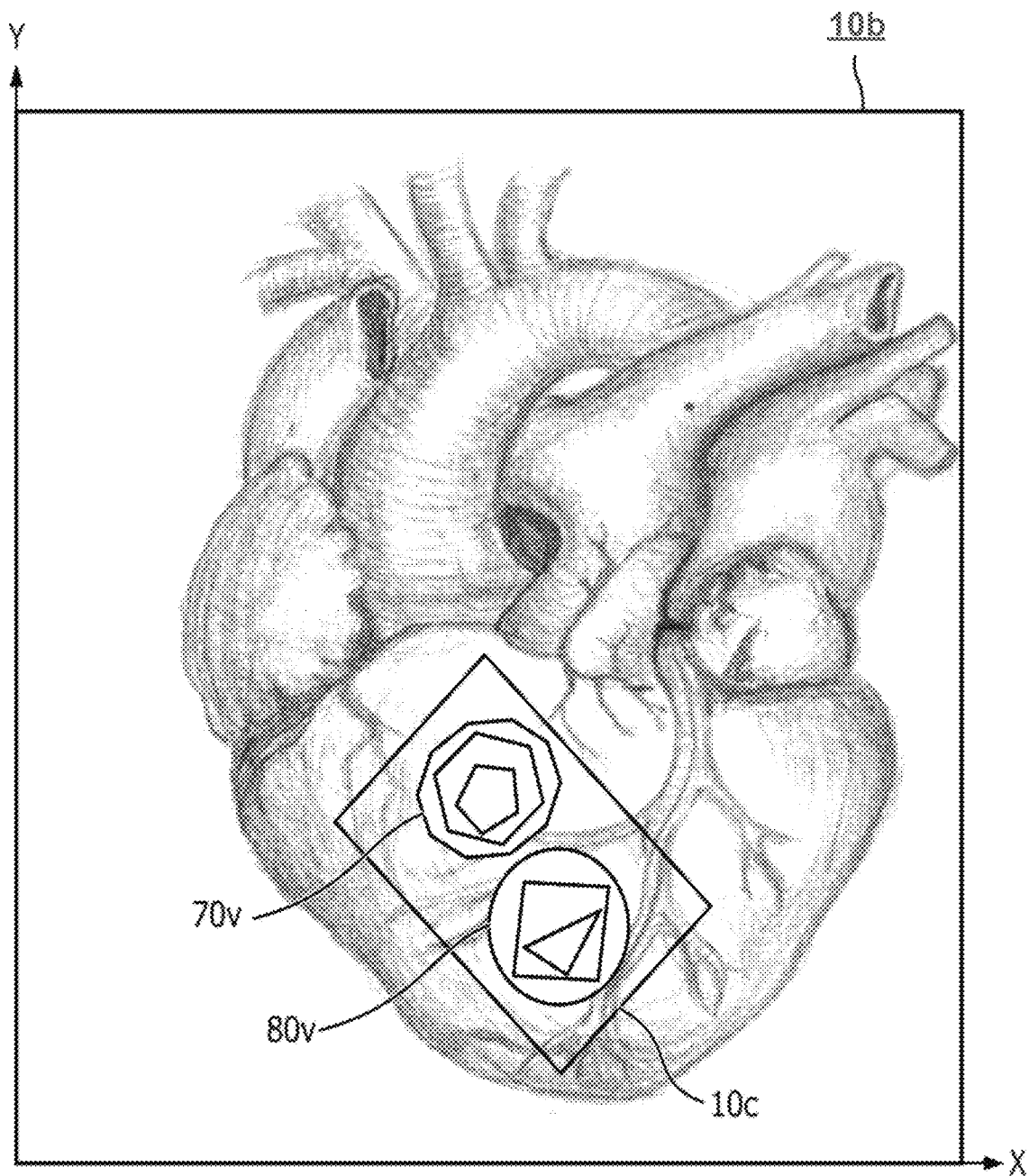
FIG. 4B illustrates an exemplary a graphical delineation mapping of a motion scale within a 3D imaging coordinate space in accordance with the inventive principles of the present disclosure.

Specifically, a stage S102 of flowchart 100 encompasses a motion scale mapping of a motion scale 70p and a motion scale 80p within an image coordinate space of pre-operative scan 12c of the heart. To this end, as known in the art of the present disclosure, stage S102 may involve a segmentation of the heart within an image coordinate space 10b of pre-operative scan 12c as best shown in FIG. 4B. Referring to FIG. 4B, a graphical user interface (not shown) is provided for allowing a graphical delineation of motion scale 70v and motion scale 80v covering a volumetric area relative to the segmented heart. Again, motion scale 70v includes three (3) zones of scaling factors covering a volumetric area as shown relative to the heart and motion scale 80v includes three (3) zones of scaling factors covering a volumetric area as shown relative to the heart.

Referring back to FIG. 4A, a stage S104 of flowchart 100 encompasses an actuation of a pair of surgical robotic arms 90a and 90b via a use input device within surgical coordinate space 13 encircling the cardiac region. Specifically, prior to entering into the field of view of the endoscope, motion of end-effectors of surgical robotic arms 90a and 90b within surgical coordinate space 13 in accordance with a default motion setting is tracked (e.g., an electromagnetic tracking, an optical tracking, a FORS sensor tracking, encoded joint tracking or image tracking). As surgical robotic arms 90*a* and 90*b* appear in intra-operative endoscopic view 12*d*, motion scales 70*v* and 80*v* are applied to the default motion setting depending on the tracked positons of the end-effectors of surgical robotic arms 90*a* and 90*b* within of surgical coordinate space 13 or image coordinate space 10*c*.

Figure 6A:
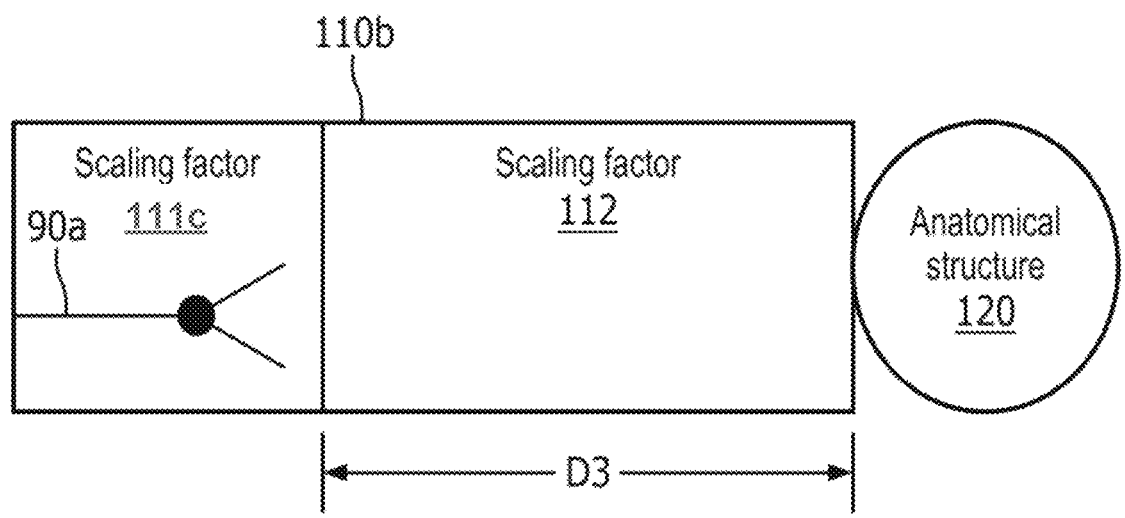
FIGS. 6A and 6B illustrates a second exemplary dynamic motion scale in accordance with the inventive principles of the present disclosure.
Figure 6B:
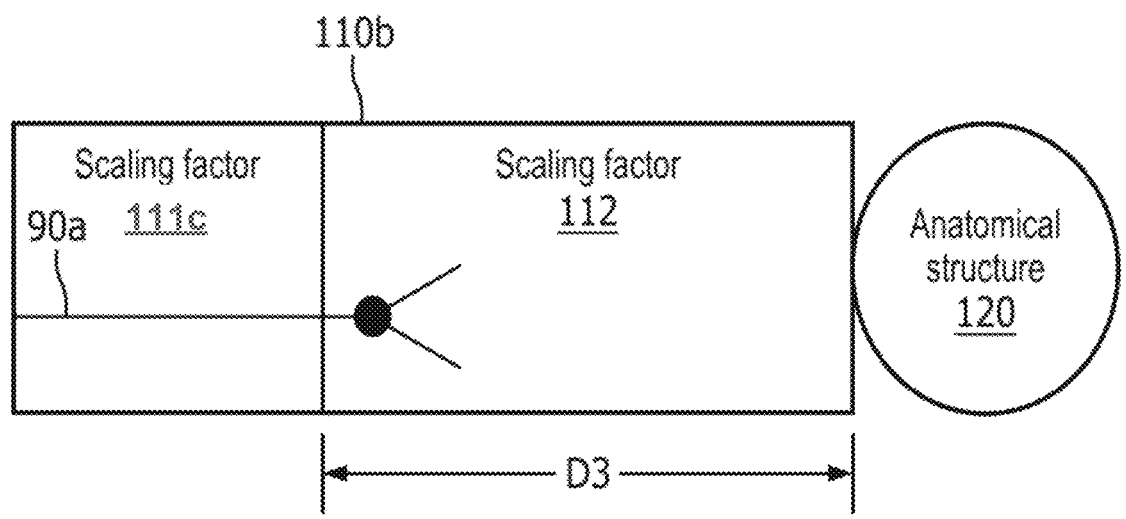
Figure 7:
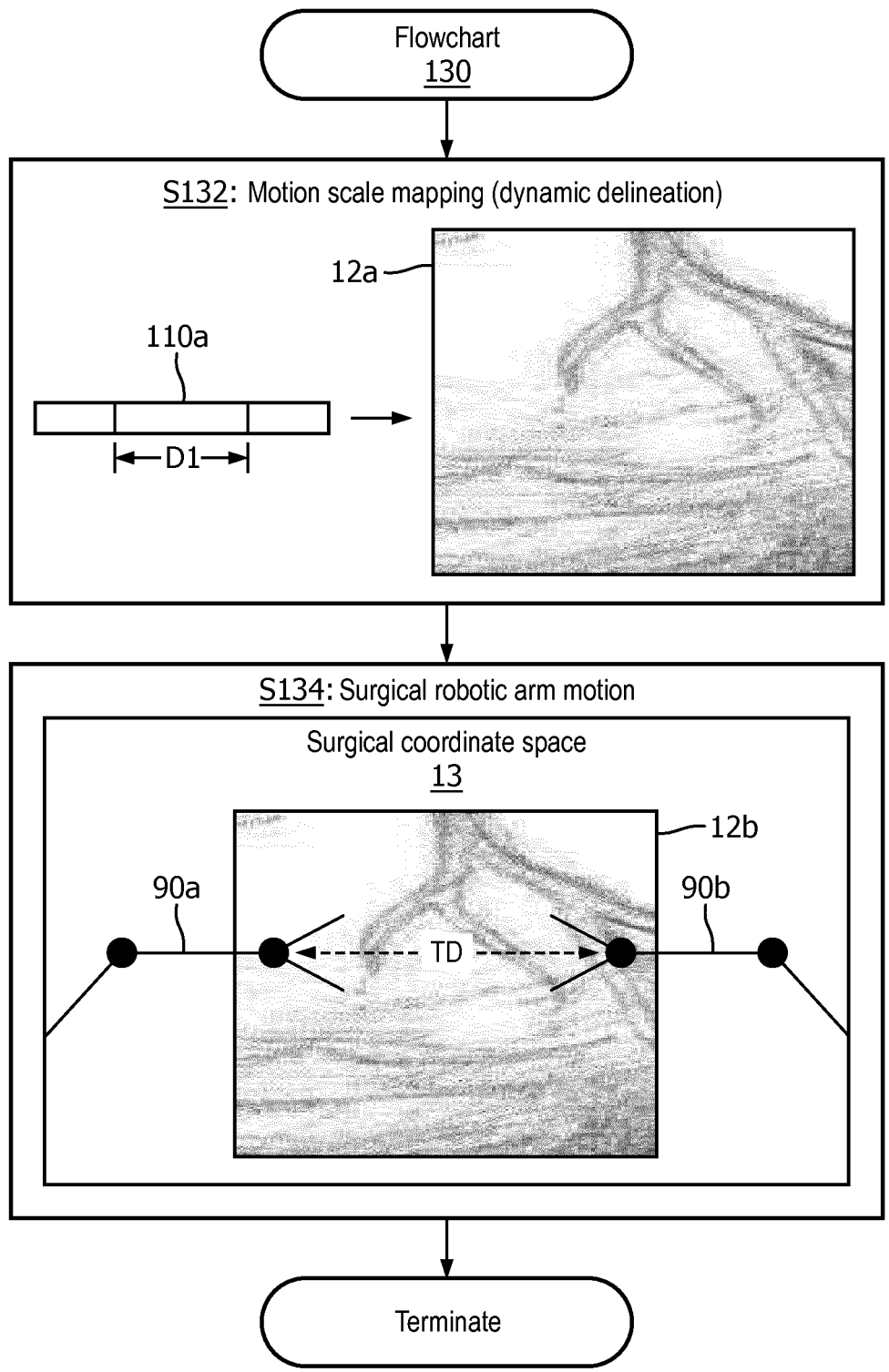
FIG. 7 illustrates a flowchart representative of a dynamic mapping of a motion scale within a two-dimensional ("2D") imaging coordinate space in accordance with the inventive principles of the present disclosure.

To facilitate a further understanding of the inventions of the present disclosure, the following description of FIGS. 5-7 teaches basic inventive principles of a dynamic mapping of a motion scale within an imaging coordinate space in accordance with the inventive principles of the present disclosure. From this description of FIGS. 5-7, those having ordinary skill in the art will appreciate how to apply the inventive principles of the present disclosure to practice numerous and various embodiments of a dynamic mapping of a motion scale within an imaging coordinate space.

Generally, a dynamic motion scale in accordance with the inventive principles of the present disclosure is linked to motions of the surgical robotic arms) and may be further linked to an anatomical structure within an image coordinate space.

Figure 5A:
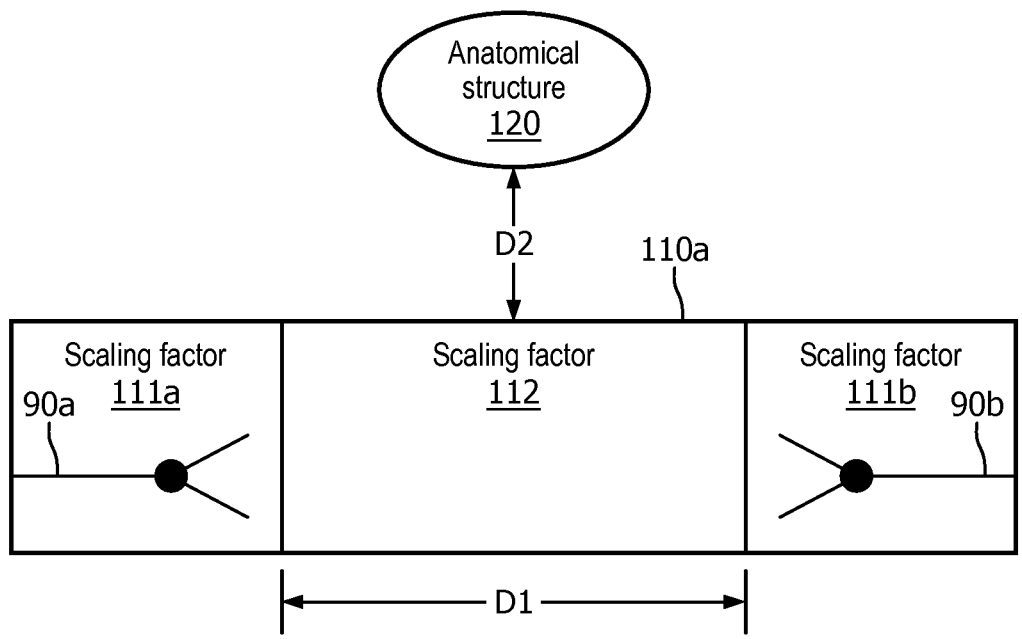
FIGS. 5A and 5B illustrate a first exemplary dynamic motion scale in accordance with the inventive principles of the present disclosure.
Figure 5B:
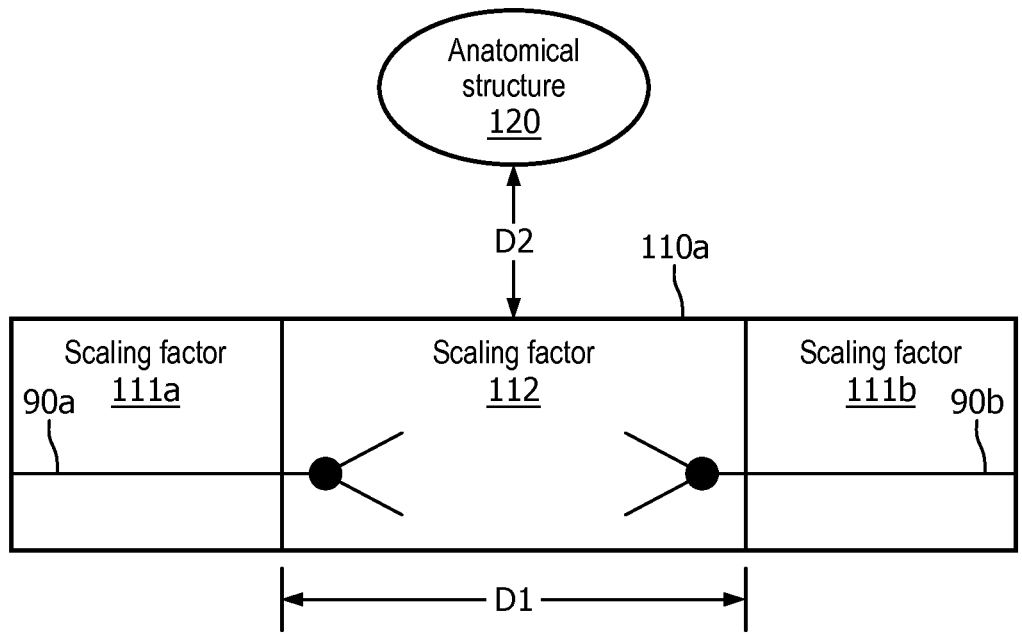

For example, referring to FIGS. 5A and 5B, a dynamic motion scale 110*a* has three (3) zones of scaling factors 111*a*, 111*b* and 112. Scaling factors 111*a* and 111*b* apply to a default motion setting of surgical robotic arms 90*a* and 90*b* when a tracked distance between surgical robotic arms 90*a* and 90*b* is greater than a distance threshold D1 as best shown in FIG. 5A. Conversely, scaling factor 112 applies when a tracked distance between surgical robotic arms 90*a* and 90*b* is less than a distance threshold D1 as best shown in FIG. 5B.

Optionally, scaling factor 112 may only apply to a default motion setting of surgical robotic arms 90*a* and 90*b* when the tracked distance between surgical robotic arms 90*a* and 90*b* is less than a distance threshold D1 and further when a tracked distance of surgical robotic 90*a* and/or surgical robotic arm 90*b* relative to an anatomical structure 120 is less than a distance threshold D2.

In practice, distance thresholds D1 and D2 may be default thresholds derived from the particular surgical robotic procedure or may be user defined via a graphical user interface.

Also in practice, scaling factors 111*a*, 111*b* and 112 may represent any factor associated with the motion of surgical robotic arm 90*a* including, but not limited to, a positioning, a velocity, an acceleration and a force as previously described herein.

By further example, referring to FIGS. 6A and 6B, a dynamic motion scale 110*b* has two (2) zones of scaling factors 111*c* and 112. Scaling factor 111*c* applies to a default motion setting of surgical robotic arms 90*a* and 90*b* when a tracked distance between surgical robotic arm 90*a* and anatomical structure 120 is greater than a distance threshold D3 as best shown in FIG. 6A. Conversely, scaling factor 112 applies when a tracked distance between surgical robotic arm 90*a* and anatomical structure 120 is less than a distance threshold D3 as best shown in FIG. 6B.

In practice, distance threshold D3 may be default thresholds derived from the particular surgical robotic procedure or may be user defined via a graphical user interface.

Referring to FIG. 7, a flowchart 130 represents an image guided motion scaled robot control method of the present disclosure involving pre-operative endoscopic view 12*a* and intra-operative endoscopic view 12*b* of a heart.

Generally, in a pre-operative phase of the surgical robotic procedure, a surgical robotic arm holding an endoscope is positioned via a user input device within a surgical coordinate space encircling a cardiac region to acquire pre-operative endoscopic view 12*a* of the heart. Thereafter, for an intra-operative phase of the surgical robotic procedure, the endoscope is held in or repositioned to the same pre-operative position to acquire an intra-operative endoscopic view 12*b* of a heart.

Specifically, a stage S132 of flowchart 130 encompasses a motion scale mapping of a motion scale 110*a* within an image coordinate space of pre-operative endoscopic view 12*a* of the heart. To this end, as known in the art of the present disclosure, stage S62 may involve a calibration of the endoscope holding surgical robotic arm and a field of view of the endoscope, and a tracking of the surgical robotic arm within the surgical coordinate space (e.g., an electromagnetic tracking, an optical tracking, a FORS sensor tracking, and encoded joint tracking). From the calibration and tracking, the endoscope holding surgical robotic arm is actuated via a user input device to a desired field of view of the endoscope for the acquisition of pre-operative endoscopic view 12*a* of the heart.

Once positioned, a graphical user interface (not shown) is provided for allowing a dynamic delineation of motion scale 110*a* within an image coordinate space outlining pre-operative endoscopic view 12*a* of the heart. More particularly, motion scale 110*a* and an application rule of motion scale 110*a* are user defined and linked to pre-operative endoscopic view 12*a* of the heart.

Still referring to FIG. 7, a stage S134 of flowchart 130 encompasses an actuation of a pair of surgical robotic arms 90*a* and 90*b* via a user input device within a 3D surgical coordinate space 13 encircling the cardiac region. Specifically, prior to entering into the field of view of the endoscope, motion of end-effectors of surgical robotic arms 90*a* and 90*b* within surgical coordinate space 13 in accordance with a default motion setting is tracked (e.g., an electromagnetic tracking, an optical tracking, a FORS sensor tracking, and encoded joint tracking).

As surgical robotic arms 90*a* and 90*b* appear in intra-operative endoscopic view 12*e*, motion scale 110*a* is applied to the default motion setting depending on a tracked distance TD between positons of the end-effectors of surgical robotic arms 90*a* and 90*b* within surgical coordinate space 13 or image coordinate space 12*b* (e.g., an electromagnetic tracking, an optical tracking, a FORS sensor tracking, encoded joint tracking or image tracking).

Figure 8:
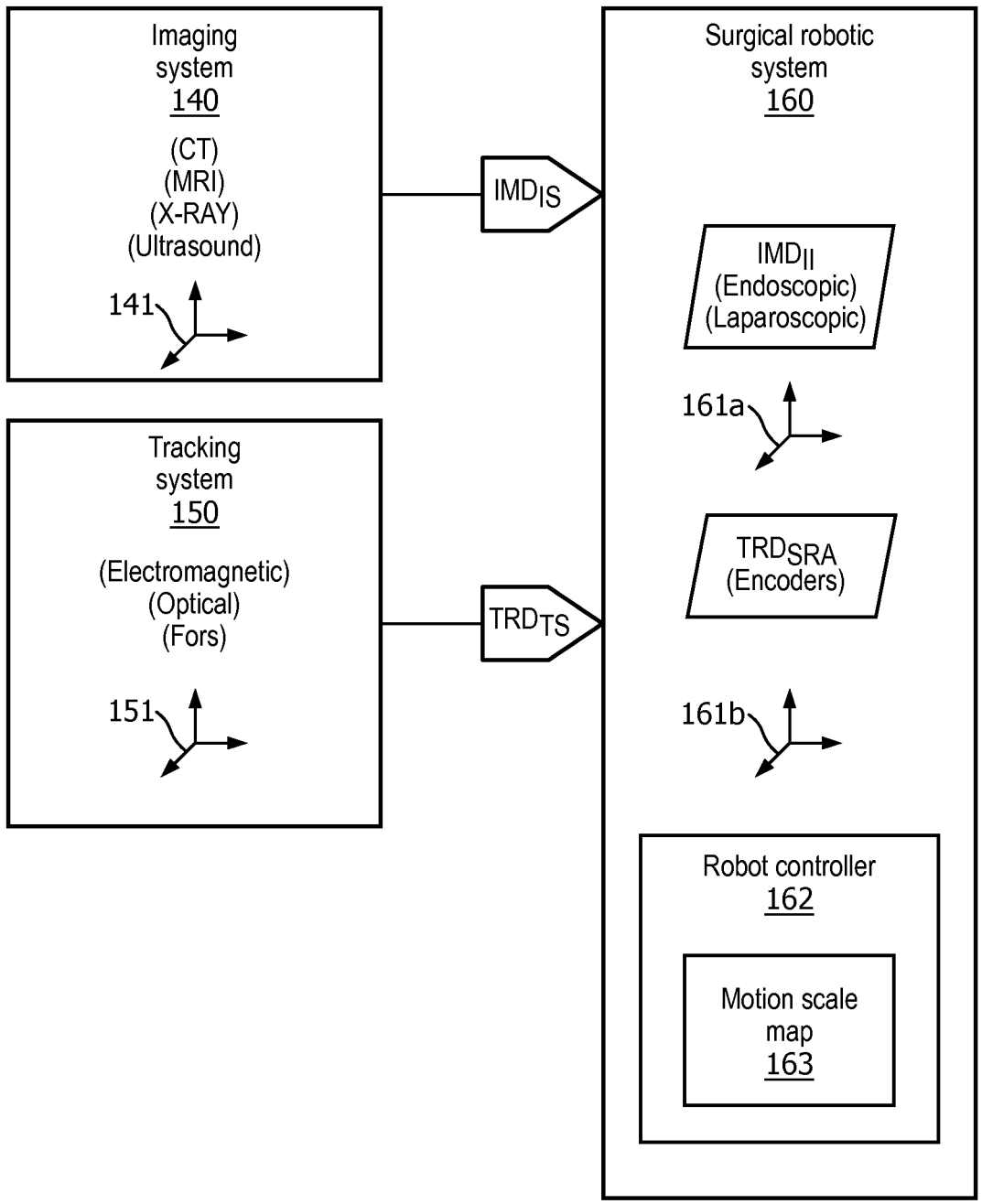
FIG. 8 illustrates an exemplary embodiment of a surgical system in accordance with the inventive principles of the present disclosure.

To facilitate a further understanding of the inventions of the present disclosure, the following description of FIGS. 8-10 teaches basic inventive principles of an image guided motion scaled surgical robotic system and an image guided motion scaled surgical robotic controller in accordance with the inventive principles of the present disclosure. From this description of FIGS. 8-10, those having ordinary skill in the art will appreciate how to apply the inventive principles of the present disclosure to practice numerous and various embodiments of an image guided motion scaled surgical robotic system and an image guided motion scaled surgical robotic controller.

Referring to FIG. 8, a surgical system of the present disclosure employs an imaging system 140, a tracking system 150 and an image guided motion scaled surgical robotic surgical robotic system 160.

Imaging system 140 implements any imaging modality, known in the art of the present disclosure and hereinafter conceived, for imaging an anatomical region (not shown) within an image coordinate system 141 and for communicating imaging data $IMD_{IS}$ informative of such imaging to image guided motion scaled surgical robotic surgical robotic system 160. Examples of the imaging modality include, but are not limited to, CT, MRI, X-ray and ultrasound.

In practice, imaging system 140 is an optional component of the surgical system and may be omitted, particularly when image guided motion scaled surgical robotic surgical robotic system 160 employs an imaging instrument held by a surgical robotic arm (not shown) for imaging the anatomical structure within an image coordinate system 161a and generating imaging data $IMD_{II}$ indicative of such imaging. Examples of such imaging instruments include, but are not limited to, an endoscope and a laparoscope.

Tracking system 150 implements any tracking technique, known in the art of the present disclosure and hereinafter conceived, for tracking a surgical robotic arm within a tracking coordinate system 151 and for communicating tracking data $TRD_{TS}$ indicative of such tracking to image guided motion scaled surgical robotic surgical robotic system 160. Examples of the tracking technique include, but are not limited to, electromagnetic, optical and FORS sensing.

In practice, tracking system 150 is an optional component of the surgical system and may be omitted, particularly when surgical robotic system 160 employs encoded surgical robots arms (not shown) generating tracking data $TRD_{SRA}$ for tracking the surgical robotic arm(s) within a surgical coordinate space 161b.

Also in practice, those having ordinary skill in the art will know how to register two or more the aforementioned coordinates spaces as needed in accordance with registration techniques known in the art of the present disclosure.

Still referring to FIG. 8, image guided motion scaled surgical robotic surgical robotic system 160 further employs an image guided motion scaled surgical robotic controller 162 having a motion scale map 163 of the present disclosure for controlling an execution of an imaging guided motion scaled robot control method of the present disclosure, such as, for example, the methods shown in FIGS. 3, 4 and 7.

In practice, surgical robotic system 160 may be embodied in numerous and various structural architectures.

Figure 9A:
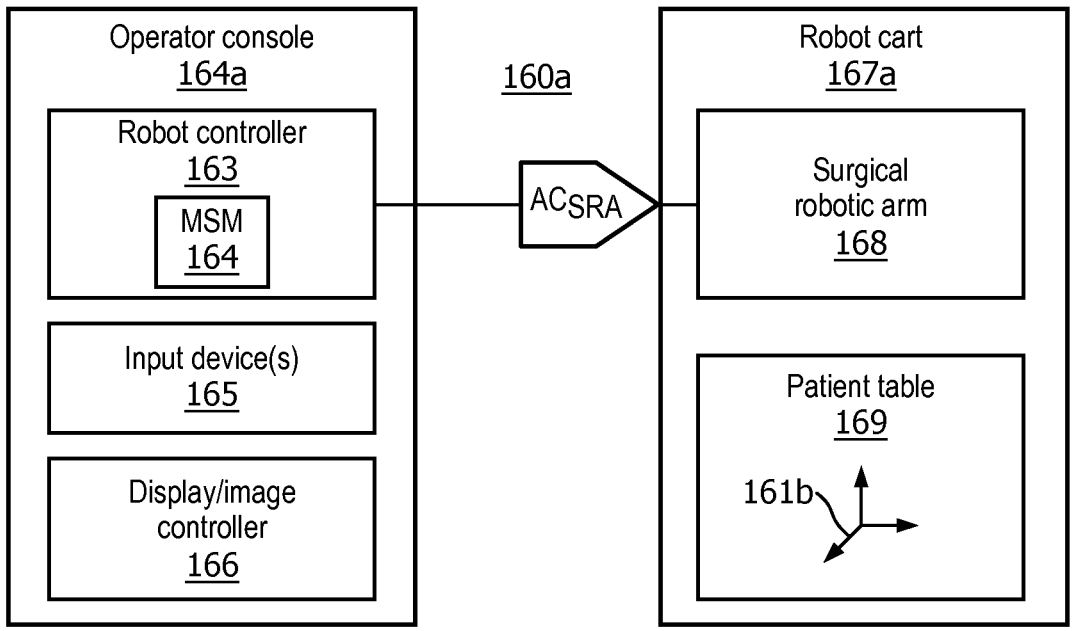
FIGS. 9A and 9B illustrate exemplary embodiments an imaged guided motion scaled surgical robotic system in accordance with the inventive principles of the present disclosure.

In one embodiment as shown in FIG. 9A, an image guided motion scaled surgical robotic system 160a has an operator console 164a and a robot cart 167a.

Referring to FIG. 9A, operator console 164a employs robot controller 162 (FIG. 8) of the present disclosure, one or more input devices 165 (e.g., handle(s), joystick(s), roller ball(s), etc.) as known in the art of the present disclosure and a display/image controller 166 as known in the art of the present disclosure.

Robot cart 167a employs one or more surgical robotic arms 168 as known in the art of the present disclosure and a patient table 169 as known in the art of the present disclosure, particularly for establishing surgical coordinate space 161b (FIG. 8).

In operation, user input device(s) 165 are manipulated to execute a user defined motion of surgical robotic arm(s) 168 within surgical coordinate space 161b via actuation commands $AC_{SRA}$ communicated by image guided motion scaled robot controller 162 to surgical robotic arm(s) 168. As previously described herein, image guided motion scaled robot controller 162 will apply motion scale map 163 to an imaging coordinate space (e.g., 161a of FIG. 8) registered to surgical robotic space 161b to thereby attenuate or amplify the user defined motion of surgical robotic arm(s) 168 within surgical coordinate space 161b in accordance with the motion scale map 163.

Figure 9B:
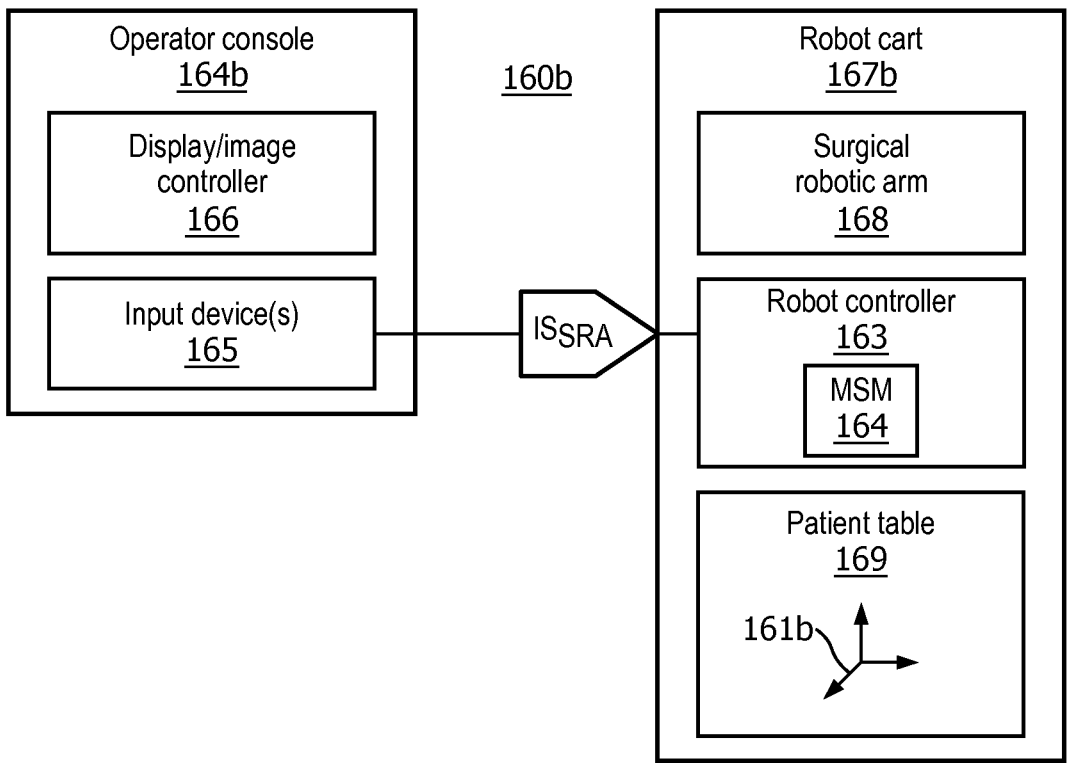

In another embodiment as shown in FIG. 9B, an image guided motion scaled surgical robotic system 160b has an operator console 164b and a robot cart 167b.

Referring to FIG. 9B, operator console 164b employs input device(s) 165 (e.g., handles) and a display/image controller 166.

Robot cart 167b employs surgical robotic arms 168, robot controller 162 (FIG. 8) and patient table 169.

In operation, user input device(s) 165 are manipulated to communicate an input signal $IS_{SRA}$ to image guided motion scaled robot controller 162 with input signal $IS_{SRA}$ being indicative of a user defined motion of surgical robotic arm(s) 168 within surgical coordinate space 161b, In response thereto, image guided motion scaled robot controller 162 communicates actuation commands $AC_{SRA}$ (not shown) to surgical robotic arm(s) 168. Again, image guided motion scaled robot controller 162 will apply motion scale map 163 to an imaging coordinate space (e.g., 161a of FIG. 8) registered to surgical robotic space 161b to thereby attenuate or amplify the user defined motion of surgical robotic arm(s) 168 within surgical coordinate space 161b in accordance with the motion scale map 163.

In practice, image guided motion scaled robot controller 162 may be embodied in numerous and various structural architectures. For example, image guided motion scaled robot controller includes a processor, a memory, a user interface, a network interface, and a storage interconnected via one or more system buses. In practice, the actual organization of the components of image guided motion scaled robot controller 162 may be more complex than illustrated.

The processor may be any hardware device capable of executing instructions stored in memory or storage or otherwise processing data. As such, the processor may include a microprocessor, field programmable gate array (FPGA), application-specific integrated circuit (ASIC), or other similar devices.

The memory may include various memories such as, for example L1, L2, or L3 cache or system memory. As such, the memory may include static random access memory (SRAM), dynamic RAM (DRAM), flash memory, read only memory (ROM), or other similar memory devices.

The user interface may include one or more devices for enabling communication with a user such as an administrator. For example, the user interface may include a display, a mouse, and a keyboard for receiving user commands. In some embodiments, the user interface may include a command line interface or graphical user interface that may be presented to a remote terminal via the network interface. The network interface may include one or more devices for enabling communication with other hardware devices. For example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon which the processor may operate. For example, the storage may store a base operating system for controlling various basic operations of the hardware. The storage may further store application module(s) in the form of executable software/firmware and/or application module(s).

Figure 10A:
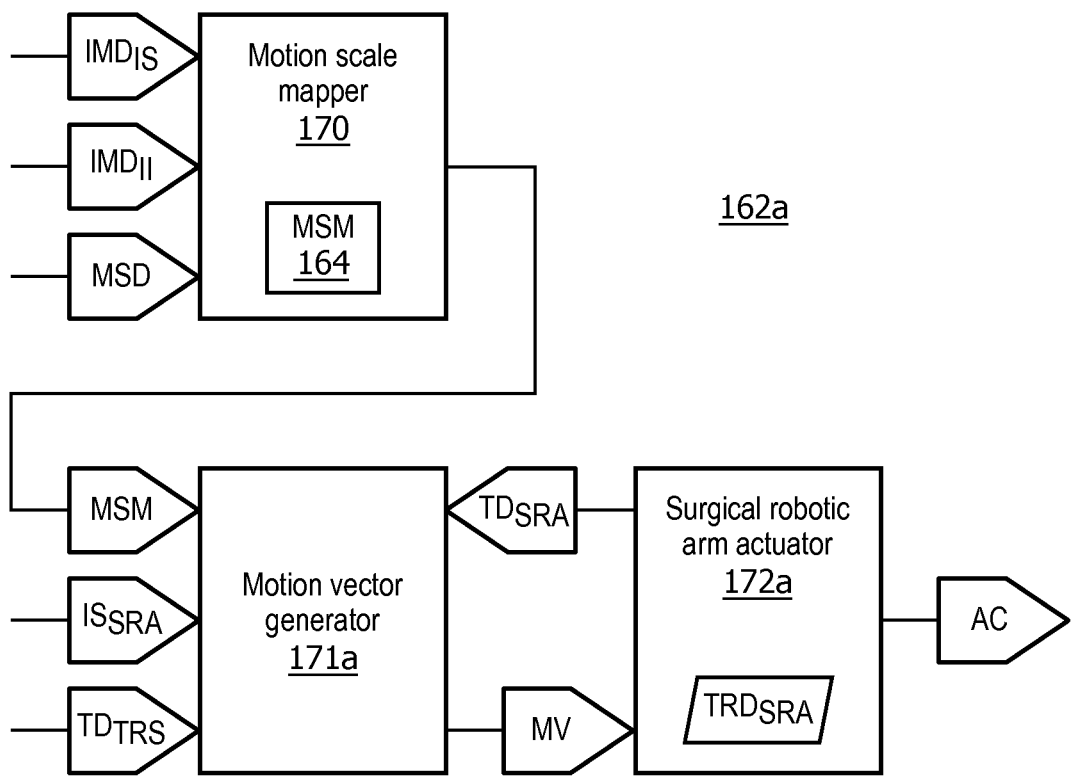
FIGS. 10A and 10B illustrate exemplary embodiments an imaged guided motion scaled robot controller in accordance with the inventive principles of the present disclosure.

In one embodiment shown in FIG. 10A, an image guided motion scaled robot controller 162a may employ application modules including a motion scale mapper 170, a motion vector generator 171a and a surgical robotic arm actuator 172a.

Referring to FIG. 10A, motion scale mapper 170 processes imaging data $IMD_{IS}$ from imaging system 140 (FIG. 8)(if employed) and/or imaging data $IMD_{II}$ from an imaging instrument (if employed)(e.g., an endoscope), and further processes a motion scale delineation signal MSD from a graphical user interface (not shown) to thereby map a motion scale within an image coordinate space as previously described herein.

Motion scale mapper 170 communicates the motion scale map MSM to motion vector generator 171a, which further processes input signal $IS_{SRA}$ from an input device (e.g., handle(s), joystick(s), roller ball(s), etc.) and tracking data $TD_{TRS}$ from tracking system 150 (if employed)(FIG. 8) to thereby generate a motion vector MV indicative of a translation, a rotation and/or a pivoting of a surgical robotic arm 168 with surgical coordinate system 161b as requested by input signal $IS_{SRA}$ and attenuated or amplified in accordance with motion scale map MSM based on tracking data $TD_{TRS}$.

Alternative to encoded tracking data $TD_{TRS}$, motion vector generator 171a may process encoded tracking data $TD_{SRA}$ from surgical robotic arm actuator 172a to thereby generate motion vector MV indicative of a translation, a rotation and/or a pivoting of surgical robotic arm 168 with surgical coordinate system 161b as requested by input signal $IS_{SRA}$ and attenuated or amplified in accordance with motion scale map MSM based on encoded tracking data $TD_{SRA}$.

Motion vector generator 171a communicates motion vector MV to surgical robotic arm actuator 172a, which generates actuation commands AC instructive of the translation, rotation and/or pivoting of surgical robotic arm 168 within surgical coordinate system 161b.

Figure 10B:
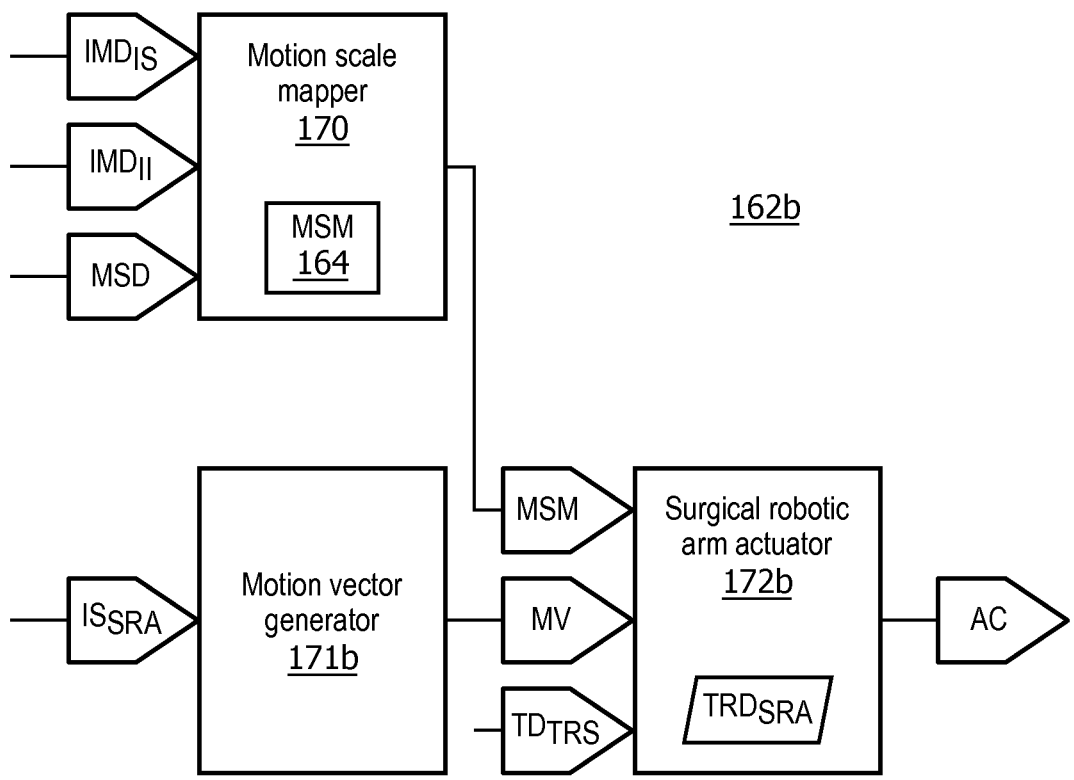

In another embodiment shown in FIG. 10B, an image guided motion scaled robot controller 162b may employ application modules including a motion scale mapper 170, a motion vector generator 171b and a surgical robotic arm actuator 172b.

Referring to FIG. 10B, as previously described, motion scale mapper 170 processes imaging data $IMD_{IS}$ from imaging system 140 (FIG. 8)(if employed) and/or imaging data $IMD_{II}$ from an imaging instrument (if employed)(e.g., an endoscope), and further processes motion scale delineation signal MSD from a graphical user interface (not shown) to thereby map a motion scale within an image coordinate space as previously described herein.

Motion vector generator 171b processes input signal $IS_{SRA}$ from an input device (e.g., handle(s), joystick(s), roller ball(s), etc.) to thereby generate a motion vector MV indicative of a translation, a rotation and/or a pivoting of surgical robotic arm 168 with surgical coordinate system 161b Motion scale mapper 170 communicates the motion scale map MSM to surgical robotic arm actuator 172b and motion vector generator 171b communicates the motion vector MV to surgical robotic arm actuator 172b, which further processes tracking data $TD_{TRS}$ from tracking system 150 (if employed)(FIG. 8) to thereby generate actuation commands AC indicative of a translation, a rotation and/or a pivoting of surgical robotic arm 168 with surgical coordinate system 161b as requested by input signal $IS_{SRA}$ and attenuated or amplified in accordance with motion scale map MSM based on tracking data $TD_{TRS}$.

Alternative to tracking data $TD_{TRS}$, surgical robotic arm actuator 172b may process encoded tracking data $TD_{SRA}$ to thereby generate actuation commands AC indicative of a translation, a rotation and/or a pivoting of surgical robotic arm 168 with surgical coordinate system 161b as requested by input signal $IS_{SRA}$ and attenuated or amplified in accordance with motion scale map MSM based on encoded tracking data $TD_{SRA}$.

Referring to FIGS. 1-10, those having ordinary skill in the art will appreciate numerous benefits of the present disclosure including, but not limited to, an improvement over surgical robot systems by the inventions of the present disclosure in providing a motion scale that depends on the environment in which the robotic arm is operating and allows for improved handling by facilitating a reduction in a risk to patient injury and a reduction in surgical procedure time.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/ or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive image guided motion scales, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An image guided motion scaled surgical robotic system, comprising:
   a surgical robotic arm; and
   an image guided motion scaled robot controller in communication with the surgical robotic arm, the image guided motion scaled robot controller structurally configured, responsive to an input signal indicative of a user defined motion of the surgical robotic arm within an anatomical region, to control an actuated motion of the surgical robotic arm within the anatomical region based on a map of a motion scale delineated within an imaging of the anatomical region.

2. The image guided motion scaled surgical robotic system of claim 1, wherein the image guided motion scaled robot controller is further structurally configured to control a delineation of the motion scale within the imaging of the anatomical region.

3. The image guided motion scaled surgical robotic system of claim 1, wherein the image guided motion scaled robot controller is further structurally configured to control a delineation of the motion scale as a function of a distance between the surgical robotic arm and an anatomical structure within the imaging of the anatomical region.

4. The image guided motion scaled surgical robotic system of claim 1, further comprising:
   an additional surgical robotic arm; and
   wherein the image guided motion scaled robot controller is further structurally configured to control a delineation of the motion scale as a function of a distance between the surgical robotic arm and the additional surgical robotic arm relative to an anatomical structure within the imaging of the anatomical region.

5. The image guided motion scaled surgical robotic system of claim 1, wherein the image guided motion scaled robot controller is further structurally configured to control the actuated motion of the surgical robotic arm within the anatomical region responsive to tracking data indicative of a tracking of the surgical robotic arm within the anatomical region.

6. The image guided motion scaled surgical robotic system of claim 1, wherein the image guided motion scaled robot controller is further structurally configured to control the actuated motion of the surgical robotic arm within the anatomical region responsive to tracking data indicative a tracking of the surgical robotic arm within the imaging of the anatomical region.

7. The image guided motion scaled surgical robotic system of claim 1, wherein the motion scale is one of a position motion scale, a velocity motion scale, an acceleration motion scale, or a force motion scale.

8. The image guided motion scaled surgical robotic system of claim 1, wherein the motion scale includes at least one scaling factor.

9. A image guided motion scaled robot controller, comprising:
   a motion vector generator structurally configured to generate a motion vector signal responsive to an input signal indicative of a user defined motion of a surgical robotic arm within an anatomical region,
      wherein the motion vector signal is indicative of an actuated motion of a surgical robotic arm within the anatomical region;
   a surgical robotic arm actuator structurally configured to generate actuation commands responsive to a generation of the motion vector signal by the motion vector generator,
      wherein the actuation commands are instructive of the actuated motion of the surgical robotic arm within the anatomical region; and
   wherein at least one of:
      the motion vector generator is further structurally configured to generate the motion vector signal based on a map of a motion scale delineated within an imaging of the anatomical region; and
      the surgical robotic arm actuator is further structurally configured to generate the actuation commands based on the motion scale delineated within an imaging of the anatomical region.

10. The image guided motion scaled surgical robotic controller of claim 9, further comprising:
    a motion scale mapper structurally configured to delineate the motion scale within the imaging coordinate space.

11. The image guided motion scaled surgical robotic controller of claim 9, further comprising:
    a motion scale mapper structurally configured to compute the motion scale as a function of a distance between the surgical robotic arm and an anatomical structure within the imaging coordinate space.

12. The image guided motion scaled surgical robotic controller of claim 9, further comprising:

a motion scale mapper structurally configured to compute the motion scale as a function of a distance between the surgical robotic arm and an additional surgical robotic arm relative to an anatomical structure within the imaging coordinate space.

13. The image guided motion scaled surgical robotic controller of claim 9, wherein at least one of:

the motion vector generator is further structurally configured to generate the motion vector signal responsive to tracking data indicative of a tracking of the surgical robotic arm within the surgical coordinate space; and the surgical robotic arm actuator is further structurally configured to generate the actuation commands responsive to the tracking data indicative of the tracking of the surgical robotic arm within the surgical coordinate space.

14. The image guided motion scaled surgical robotic controller of claim 9, wherein at least one of:

the motion vector generator is further structurally configured to generate the motion vector signal responsive to tracking data indicative of a tracking of the surgical robotic arm within the imaging coordinate space; and the surgical robotic arm actuator is further structurally configured to generate the actuation commands responsive to tracking data indicative of the tracking within the imaging coordinate space.

15. The image guided motion scaled surgical robotic controller of claim 9, wherein the motion scale is one of a position motion scale, a velocity motion scale, an acceleration motion scale, or a force motion scale.

16. An image guided motion scaled surgical robot control method comprising:

providing an image guided motion scaled surgical robotic system including a surgical robotic arm and an image guided motion scaled robot controller;

receiving, by the image guided motion scaled robot controller, an input signal indicative of a user defined motion of the surgical robotic arm within an anatomical region; and responsive to the input signal, controlling, by the image guided motion scaled robot controller, an actuated motion of the surgical robotic arm within the anatomical region based on a map of a motion scale delineated within an imaging of the anatomical region.

17. The method of claim 16, further comprising:

controlling, by the image guided motion scaled robot controller, a delineation of the motion scale within the imaging coordinate space.

18. The motion dependency robot control method of claim 16, further comprising:

controlling, by the image guided motion scaled robot controller, a delineation of the motion scale as a function of a distance between the surgical robotic arm and an anatomical structure within the imaging coordinate space.

19. The method of claim 16, further comprising:

controlling, by the image guided motion scaled robot controller, a delineation of the motion scale as a function of a distance between the surgical robotic arm and an additional surgical robotic arm relative to an anatomical structure within the imaging coordinate space.

20. The method of claim 16, wherein the controlling by the image guided motion scaled robot controller of the actuated motion of the surgical robotic arm within the surgical coordinate space is responsive to tracking data indicative of at least one of:

a tracking of the surgical robotic arm within the anatomical region; and a tracking of the surgical robotic arm within the imaging of the anatomical region.

* * * * *